(12) United States Patent
Komuro et al.

(10) Patent No.: US 12,727,745 B2
(45) Date of Patent: Sep. 8, 2026

(54) MANIPULATOR SYSTEM, MANIPULATOR SYSTEM CONTROL METHOD, AND MANIPULATOR SYSTEM CONTROL DEVICE

(71) Applicant: OLYMPUS MEDICAL SYSTEMS CORP., Tokyo (JP)

(72) Inventors: Takahiro Komuro, Tokyo (JP); Kosuke Kishi, Tokyo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 310 days.

(21) Appl. No.: 18/542,640

(22) Filed: Dec. 16, 2023

(65) Prior Publication Data

US 2024/0115117 A1 Apr. 11, 2024

Related U.S. Application Data

(63) Continuation of application No. PCT/JP2021/030310, filed on Aug. 19, 2021.

(51) Int. Cl.
*A61B 1/005* (2006.01)
*A61B 1/00* (2006.01)
*A61B 90/00* (2016.01)

(52) U.S. Cl.
CPC ........ *A61B 1/0052* (2013.01); *A61B 1/00006* (2013.01); *A61B 1/0057* (2013.01); *A61B 2090/066* (2016.02)

(58) Field of Classification Search
CPC . A61B 1/00133; A61B 1/0016; A61B 1/0057; A61B 1/00112; A61B 1/00124;
(Continued)

(56) References Cited

U.S. PATENT DOCUMENTS

2007/0232856 A1* 10/2007 Ueno ..................... A61B 1/009 600/145
2016/0256071 A1 9/2016 Shelton, IV et al.
(Continued)

FOREIGN PATENT DOCUMENTS

EP 4 091 530 A1 11/2022
JP H04-241829 A 8/1992
(Continued)

OTHER PUBLICATIONS

International Search Report dated Nov. 16, 2021 received in PCT/JP2021/030310.

*Primary Examiner* — Anh Tuan T Nguyen
*Assistant Examiner* — Li-Ting Song
(74) *Attorney, Agent, or Firm* — Scully, Scott, Murphy & Presser, P.C.

(57) ABSTRACT

A manipulator system includes: a manipulator; a driving device to which the manipulator is detachably connected and which electrically drives the manipulator; a control device; a first sensor provided in the driving device; and a second sensor provided in the manipulator or the driving device. The control device is configured to perform a first step of confirming that the driving device operates normally according to electric power on the basis of an output of the first sensor, and a second step of confirming that the manipulator is connected to the driving device on the basis of an output of the second sensor. The first step includes checking whether the first sensor is normal, and the second step includes checking whether the second sensor is normal on the basis of the output of the first sensor that has been confirmed to be normal and the output of the second sensor.

16 Claims, 18 Drawing Sheets

(58) Field of Classification Search
CPC .............. A61B 1/0052; A61B 1/00006; A61B 2090/066
See application file for complete search history.

(56) References Cited

U.S. PATENT DOCUMENTS

| | | | | |
|---|---|---|---|---|
| 2016/0256156 | A1 | 9/2016 | Shelton, IV et al. | |
| 2016/0256187 | A1 | 9/2016 | Shelton, IV et al. | |
| 2018/0085178 | A1* | 3/2018 | Komuro | A61B 34/35 |
| 2019/0200895 | A1 | 7/2019 | Shelton, IV et al. | |
| 2020/0100699 | A1 | 4/2020 | Shelton, IV et al. | |
| 2022/0330790 | A1 | 10/2022 | Kambe et al. | |
| 2022/0338715 | A1 | 10/2022 | Yoshimura et al. | |
| 2022/0338720 | A1 | 10/2022 | Inoue et al. | |
| 2022/0409013 | A1 | 12/2022 | Kambe et al. | |
| 2022/0409014 | A1 | 12/2022 | Komuro et al. | |
| 2022/0409018 | A1 | 12/2022 | Sawada et al. | |
| 2022/0409024 | A1 | 12/2022 | Kambe et al. | |
| 2022/0409026 | A1 | 12/2022 | Komuro et al. | |
| 2022/0409327 | A1 | 12/2022 | Yanagawa et al. | |
| 2023/0157770 | A1* | 5/2023 | Deane | A61B 34/30<br>700/245 |
| 2023/0165644 | A1* | 6/2023 | Deane | A61B 1/0016<br>700/245 |
| 2023/0301488 | A1* | 9/2023 | Aklivanh | A61B 1/00006 |

FOREIGN PATENT DOCUMENTS

| | | | |
|---|---|---|---|
| JP | H06-189897 | A | 7/1994 |
| JP | H06-304126 | A | 11/1994 |
| JP | 2000-316803 | A | 11/2000 |
| JP | 2020-185438 | A | 11/2020 |
| WO | 2016/144601 | A1 | 9/2016 |
| WO | 2016/144689 | A1 | 9/2016 |
| WO | 2021/145051 | A1 | 7/2021 |
| WO | 2021/145411 | A1 | 7/2021 |
| WO | 2021/145423 | A1 | 7/2021 |
| WO | 2023/163216 | A1 | 8/2023 |

* cited by examiner

| | | |
|---|---|---|
| DRIVING-DEVICE STARTING SEQUENCE (S1) | START DRIVING DEVICE (S11) | |
| | SELF-DIAGNOSIS OF DRIVING DEVICE (S12) (INSPECTION OF CPU, MOTOR, ENCODER, TORQUE SENSOR) | ENCODER (DUPLICATED)<br>TORQUE SENSOR |
| MANIPULATOR CONNECTING SEQUENCE (S2) | CONFIRM CONNECTION BETWEEN MANIPULATOR AND DRIVING DEVICE (S21) | ATTACHMENT/DETACHMENT SENSOR (DUPLICATED) |
| | CONFIRM COUPLING BETWEEN BENDING WIRE AND MOTOR (S22) | COUPLING SENSOR |
| | INSPECT COUPLING SENSOR (S23) | COUPLING SENSOR<br>TORQUE SENSOR |
| | INSPECT POWER TRANSMISSION MECHANISM IN DRIVING DEVICE (S24) | TORQUE SENSOR |
| BENDING-PORTION INITIALIZATION SEQUENCE (S3) | INITIALIZE BENDING ANGLE (S31) | TENSION SENSOR |
| | APPLY INITIAL TENSION (S32) | TENSION SENSOR |
| | INSPECT TENSION SENSOR (S33) | TENSION SENSOR<br>TORQUE SENSOR |
| | INSPECT POWER TRANSMISSION MECHANISM IN MANIPULATOR (S34) | TENSION SENSOR |
| BENDING-PORTION CALIBRATION SEQUENCE (S4) | | IMAGE<br>ENCODER |

FIG. 10

| | | |
|---|---|---|
| DRIVING-DEVICE STARTING SEQUENCE (S1) | START DRIVING DEVICE (S11) | |
| | SELF-DIAGNOSIS OF DRIVING DEVICE (S12) (INSPECTION OF CPU, MOTOR, ENCODER, TORQUE SENSOR) | ENCODER (DUPLICATED)) TORQUE SENSOR |
| MANIPULATOR CONNECTING SEQUENCE (S2) | CONFIRM CONNECTION BETWEEN MANIPULATOR AND DRIVING DEVICE (S21) | ATTACHMENT/DETACHMENT SENSOR (DUPLICATED) |
| | INSPECT TENSION SENSOR (S25) | TENSION SENSOR |
| | CONFIRM COUPLING BETWEEN BENDING WIRE AND MOTOR (S22') | TENSION SENSOR TORQUE SENSOR |
| | INSPECT POWER TRANSMISSION MECHANISM IN DRIVING DEVICE (S24) | TORQUE SENSOR |
| BENDING-PORTION INITIALIZATION SEQUENCE (S3) | INITIALIZE BENDING ANGLE (S31) | TENSION SENSOR |
| | APPLY INITIAL TENSION (S32) | TENSION SENSOR |
| | INSPECT TENSION SENSOR (S33) | TENSION SENSOR TORQUE SENSOR |
| | INSPECT POWER TRANSMISSION MECHANISM IN MANIPULATOR (S34) | TENSION SENSOR |
| BENDING-PORTION CALIBRATION SEQUENCE (S4) | | IMAGE ENCODER |

FIG. 12

| | | |
|---|---|---|
| DRIVING-DEVICE STARTING SEQUENCE (S1) | START DRIVING DEVICE (S11) | |
| | SELF-DIAGNOSIS OF DRIVING DEVICE (S12) (INSPECTION OF CPU, MOTOR, ENCODER, TORQUE SENSOR) | ENCODER (DUPLICATED)<br>TORQUE SENSOR |
| MANIPULATOR CONNECTING SEQUENCE (S2) | CONFIRM CONNECTION BETWEEN MANIPULATOR AND DRIVING DEVICE (S21) | ATTACHMENT/DETACHMENT SENSOR (DUPLICATED) |
| | INSPECT TORQUE SENSOR (S26) | TORQUE SENSOR<br>CURRENT SENSOR |
| | CONFIRM COUPLING BETWEEN BENDING WIRE AND MOTOR (S22″) | TORQUE SENSOR |
| | INSPECT POWER TRANSMISSION MECHANISM IN DRIVING DEVICE (S24) | TORQUE SENSOR |
| BENDING-PORTION INITIALIZATION SEQUENCE (S3) | INITIALIZE BENDING ANGLE (S31) | TENSION SENSOR |
| | APPLY INITIAL TENSION (S32) | TENSION SENSOR |
| | INSPECT TORQUE SENSOR (S35) | TORQUE SENSOR<br>CURRENT SENSOR |
| | INSPECT POWER TRANSMISSION MECHANISM IN MANIPULATOR (S34) | TENSION SENSOR |
| BENDING-PORTION CALIBRATION SEQUENCE (S4) | | IMAGE<br>ENCODER |

FIG. 15

| | | |
|---|---|---|
| DRIVING-DEVICE STARTING SEQUENCE (S1) | START DRIVING DEVICE (S11) | |
| | SELF-DIAGNOSIS OF DRIVING DEVICE (S12) (INSPECTION OF CPU, MOTOR, ENCODER, TORQUE SENSOR) | ENCODER (DUPLICATED)<br>TORQUE SENSOR |
| MANIPULATOR CONNECTING SEQUENCE (S2) | CONFIRM CONNECTION BETWEEN MANIPULATOR AND DRIVING DEVICE (S21') | ATTACHMENT/ DETACHMENT SENSOR<br>ANTAGONISTIC SENSOR |
| | CONFIRM COUPLING BETWEEN BENDING WIRE AND MOTOR (S22) | COUPLING SENSOR |
| | INSPECT COUPLING SENSOR (S23) | COUPLING SENSOR<br>TORQUE SENSOR |
| | INSPECT POWER TRANSMISSION MECHANISM IN DRIVING DEVICE (S24) | TORQUE SENSOR |
| BENDING-PORTION INITIALIZATION SEQUENCE (S3) | INITIALIZE BENDING ANGLE (S31) | TENSION SENSOR |
| | APPLY INITIAL TENSION (S32) | TENSION SENSOR |
| | INSPECT TENSION SENSOR (S33) | TENSION SENSOR<br>TORQUE SENSOR |
| | INSPECT POWER TRANSMISSION MECHANISM IN MANIPULATOR (S34) | TENSION SENSOR |
| BENDING-PORTION CALIBRATION SEQUENCE (S4) | | IMAGE<br>ENCODER |

MANIPULATOR SYSTEM, MANIPULATOR SYSTEM CONTROL METHOD, AND MANIPULATOR SYSTEM CONTROL DEVICE

CROSS-REFERENCE TO RELATED APPLICATIONS

This is a continuation of International Application PCT/JP2021/030310 which is hereby incorporated by reference herein in its entirety.

TECHNICAL FIELD

The present invention relates to a manipulator system, a manipulator system control method, and a manipulator system control device.

BACKGROUND ART

A conventional electrically actuated medical device is provided with sensors for confirming that the medical device operates normally (for example, see PTL 1). To ensure normal operation of the medical device, the sensors are usually duplicated. For example, in an electrically actuated surgical instrument described in PTL 1, two sets formed of a motor position sensor and a processor are provided for one motor, and, when the value of at least one of the two motor position sensors is not normal, at least one processor stops the motor.

CITATION LIST

Patent Literature

{PTL 1} Japanese Unexamined Patent Application, Publication No. 2020-185438

SUMMARY OF INVENTION

According to one aspect of the present invention, there is provided a manipulator system including: a manipulator; a driving device to which the manipulator is detachably connected and which electrically drives the manipulator; a control device configured to control the manipulator and the driving device; a first sensor provided in the driving device; and a second sensor provided in one of the manipulator and the driving device. The control device is configured to perform a first step of confirming that the driving device operates normally according to electric power on the basis of an output of the first sensor, and a second step of confirming that the manipulator is connected to the driving device on the basis of an output of the second sensor. The first step includes checking whether the first sensor is normal. The second step includes checking whether the second sensor is normal on the basis of the output of the first sensor that has been confirmed to be normal in the first step and the output of the second sensor.

According to another aspect of the present invention, there is provided a control method for controlling a manipulator system, the manipulator system including a manipulator and a driving device to which the manipulator is detachably connected and which electrically drives the manipulator, the control method including: performing a first step of confirming that the driving device operates normally according to electric power on the basis of an output of a first sensor; and performing a second step of confirming that the manipulator is connected to the driving device on the basis of an output of a second sensor. The first step includes checking whether the first sensor is normal. The second step includes checking whether the second sensor is normal on the basis of the output of the first sensor that has been confirmed to be normal in the first step and the output of the second sensor.

According to another aspect of the present invention, there is provided a control device for controlling a manipulator system, the manipulator system including a manipulator and a driving device to which the manipulator is detachably connected and which electrically drives the manipulator. The control device is configured to perform a first step of confirming that the driving device operates normally according to electric power on the basis of an output of a first sensor, and a second step of confirming that the manipulator is connected to the driving device on the basis of an output of a second sensor. The first step includes checking whether the first sensor is normal. The second step includes checking whether the second sensor is normal on the basis of the output of the first sensor that has been confirmed to be normal in the first step and the output of the second sensor.

BRIEF DESCRIPTION OF DRAWINGS

FIG. 3B illustrates the configuration of the wire attachment/detachment part and the wire driving part, in a state in which the wire attachment/detachment part is connected to the wire driving part.

FIG. 7 is a table illustrating a manipulator control method according to the first embodiment, the table describing steps performed in each sequence and sensors used in each step.

FIG. 10 is a table illustrating a manipulator control method according to a second embodiment, the table describing steps performed in each sequence and sensors used in each step.

FIG. 12 is a table illustrating a manipulator control method according to a third embodiment, the table describing steps performed in each sequence and sensors used in each step.

FIG. 15 is a table illustrating a manipulator control method according to a fourth embodiment, the table describing steps performed in each sequence and sensors used in each step.

DESCRIPTION OF EMBODIMENTS

First Embodiment

A manipulator system control method, a manipulator system control device, and a manipulator system according to a first embodiment of the present invention will be described with reference to the drawings.

Figure 1:
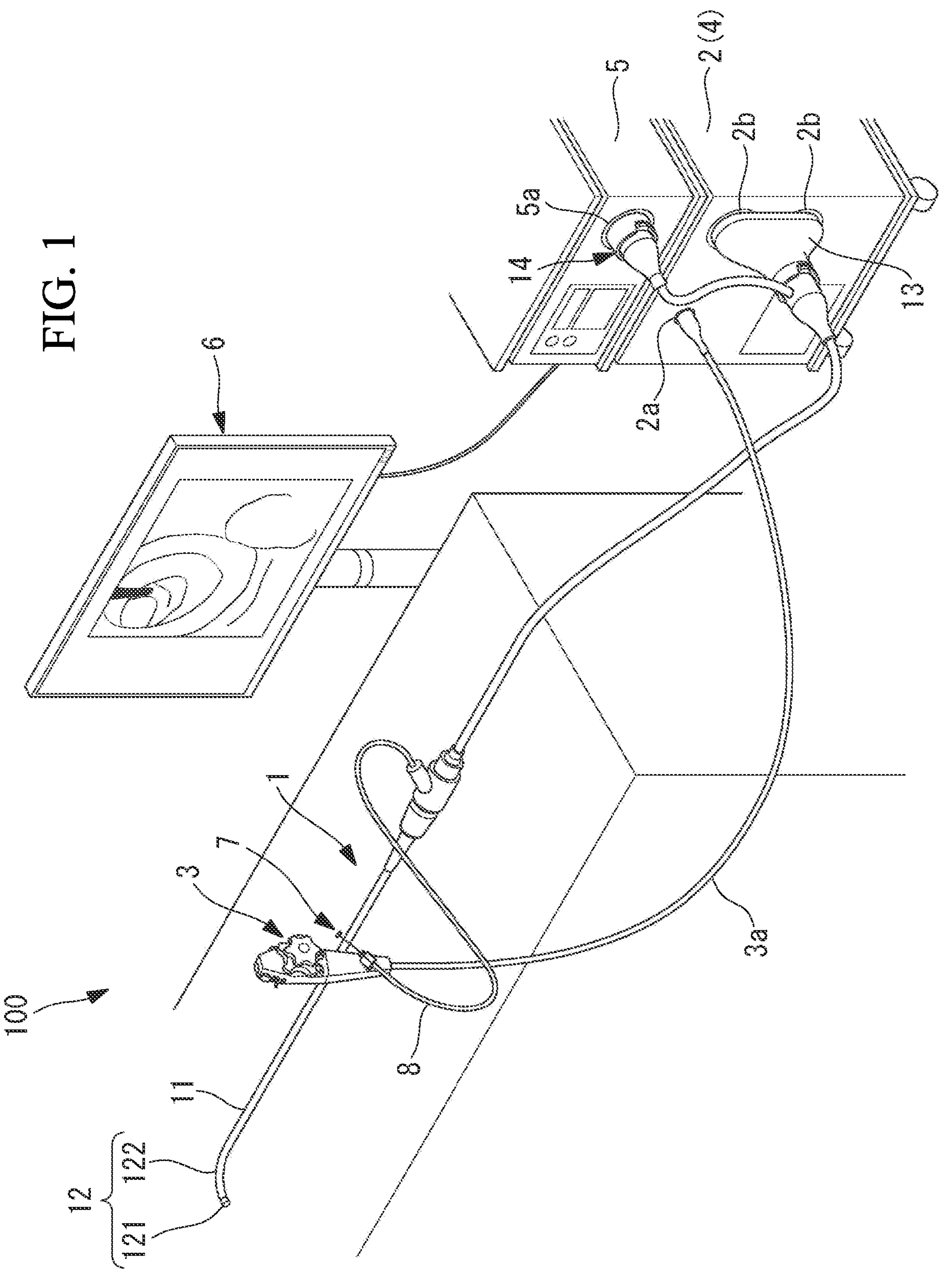
FIG. 1 illustrates the overall configuration of a manipulator system according to a first embodiment.

As illustrated in FIG. 1, a manipulator system 100 according to this embodiment includes an electrically actuated manipulator 1, a driving device 2 to which the manipulator 1 is detachably connected and which electrically drives the manipulator 1, an operation device 3 via which an operator inputs an operation for driving the manipulator 1, a control device 4 for controlling the manipulator 1 and the driving device 2, an image processor 5, and a display device 6.

The manipulator 1 is an electrically actuated flexible endoscope, a laparoscope (rigid endoscope), or a medical manipulator having an end effector or an arm at the distal end thereof to be inserted into a body cavity of a patient. Hereinbelow, the manipulator 1 will be described by taking an electrically actuated flexible endoscope as an example. In the case where the manipulator 1 is an electrically actuated endoscope, a treatment instrument 7 is inserted into the manipulator 1 via an extension tube 8. An endoscopic image acquired by the manipulator 1 is inputted to the display device 6 via the image processor 5 and is displayed on the display device 6.

The operation device 3 is connected to an adapter 2*a* of the driving device 2 via an operation cable 3*a*, and an operation input inputted to the operation device 3 is inputted from the operation device 3 to the driving device 2. The control device 4 incorporated in the driving device 2 controls the driving device 2 according to the operation input to operate the manipulator 1 according to the operation input.

Figure 2:
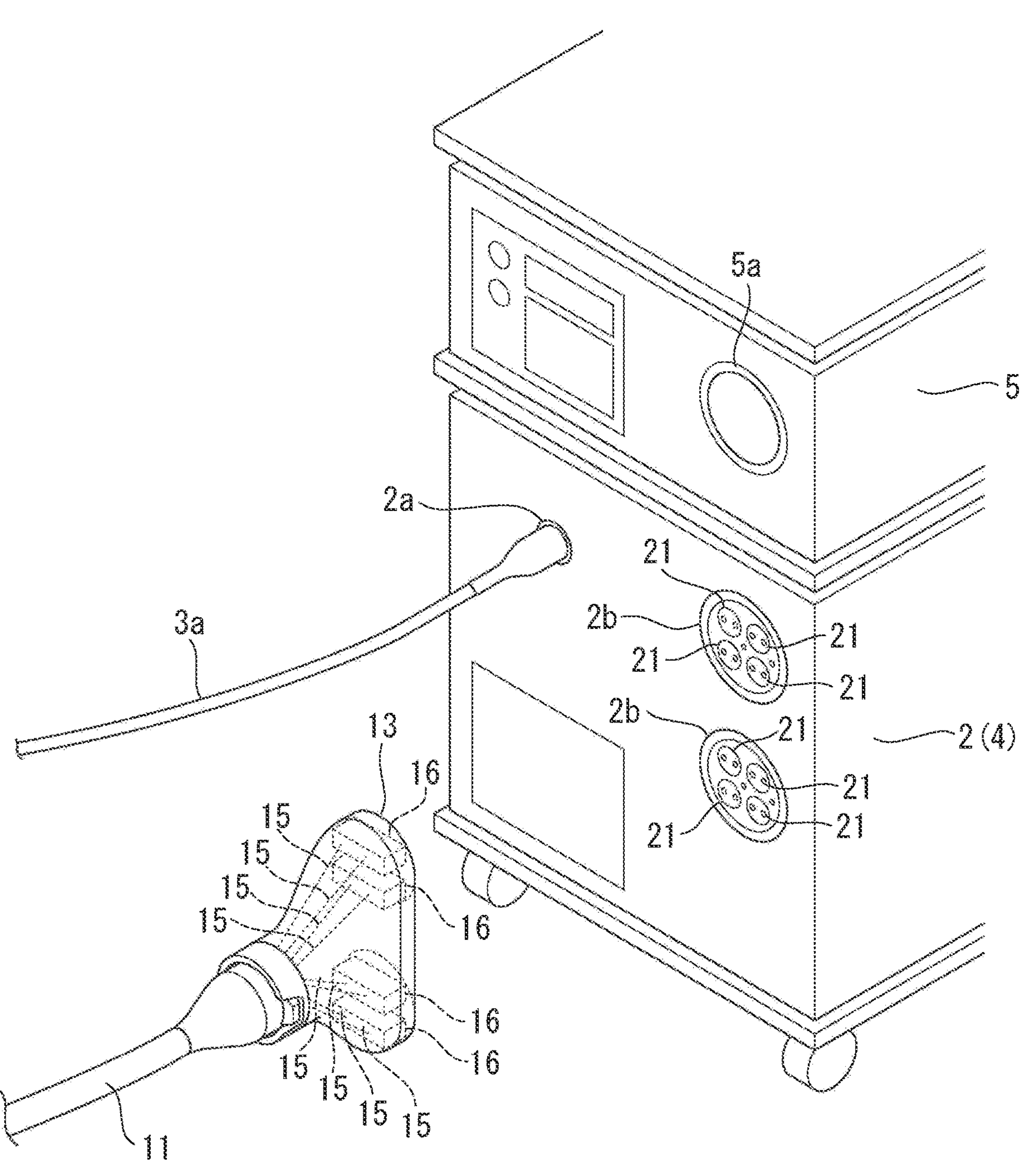
FIG. 2 is a partial diagram illustrating connection between a manipulator and a driving device.

As illustrated in FIGS. 1 and 2, the manipulator 1 includes: an insertion part 11 having a bending portion (movable portion) 12; a first attachment/detachment part 13 provided at the proximal end of the insertion part 11 and connected to adapters 2*b* of the driving device 2; a second attachment/detachment part 14 provided at the proximal end of the insertion part 11 and connected to an adapter 5*a* of the image processor 5; and a plurality of bending wires (driving wires) 15 extending from the first attachment/detachment part 13 to the bending portion 12 and transmitting driving forces from the driving device 2 to the bending portion 12.

The insertion part 11 is a long, flexible member, and the bending portion 12 is provided at the distal end of the insertion part 11. The plurality of bending wires 15 are disposed in an internal path (not illustrated) formed in the insertion part 11 and extending in the longitudinal direction of the insertion part 11.

The bending portion 12 includes a first bending portion (movable portion) 121 and a second bending portion (movable portion) 122 provided on the proximal side of the first bending portion 121. The first bending portion 121 and the second bending portion 122 are each bendable upward, downward, leftward, and rightward. Four bending wires 15 each configured to bend the first bending portion 121 upward, downward, leftward, or rightward are connected to the first bending portion 121. Four bending wires 15 each configured to bend the second bending portion 122 upward, downward, leftward, or rightward are connected to the second bending portion 122.

As illustrated in FIG. 2, the first attachment/detachment part 13 includes four wire attachment/detachment parts 16, which are mechanisms for attaching and detaching the bending wires 15 to and from the driving device 2. Each wire attachment/detachment part 16 is provided at the proximal end of a pair of bending wires 15, and attaches and detaches the pair of bending wires 15 to and from the driving device 2. For example, the four wire attachment/detachment parts 16 attach and detach, to and from the driving device 2, a pair of bending wires 15 for bending the first bending portion 121 vertically, a pair of bending wires 15 for bending the first bending portion 121 horizontally, a pair of bending wires 15 for bending the second bending portion 122 vertically, and a pair of bending wires 15 for bending the second bending portion 122 horizontally.

The driving device 2 is connected to a power source (not illustrated) and is operated by electric power supplied from the power source. The driving device 2 includes four wire driving parts 21, which are mechanisms for driving the bending wires 15. By connecting the first attachment/detachment part 13 to the adapters 2*b*, the four wire driving parts 21 are coupled to the four wire attachment/detachment parts 16 and can drive the pairs of bending wires 15. For example, the four wire driving parts 21 each drive the corresponding one of the pair of bending wires 15 for bending the first bending portion 121 vertically, the pair of bending wires 15 for bending the first bending portion 121 horizontally, the pair of bending wires 15 for bending the second bending portion 122 vertically, and the pair of bending wires 15 for bending the second bending portion 122 horizontally.

Figure 3A:
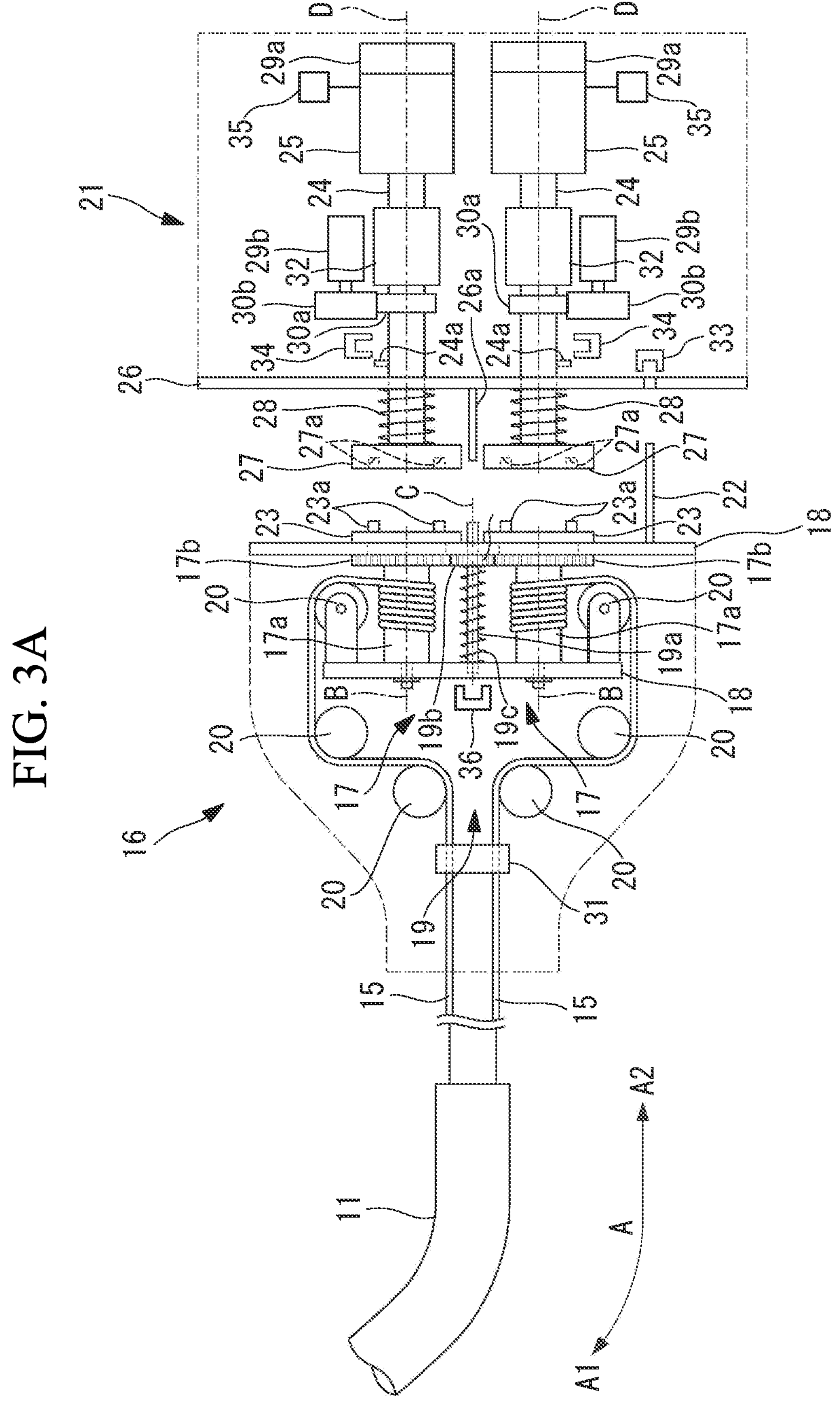
FIG. 3A illustrates the configuration of a wire attachment/detachment part and a wire driving part, in a state in which the wire attachment/detachment part is detached from the wire driving part.
Figure 3B:
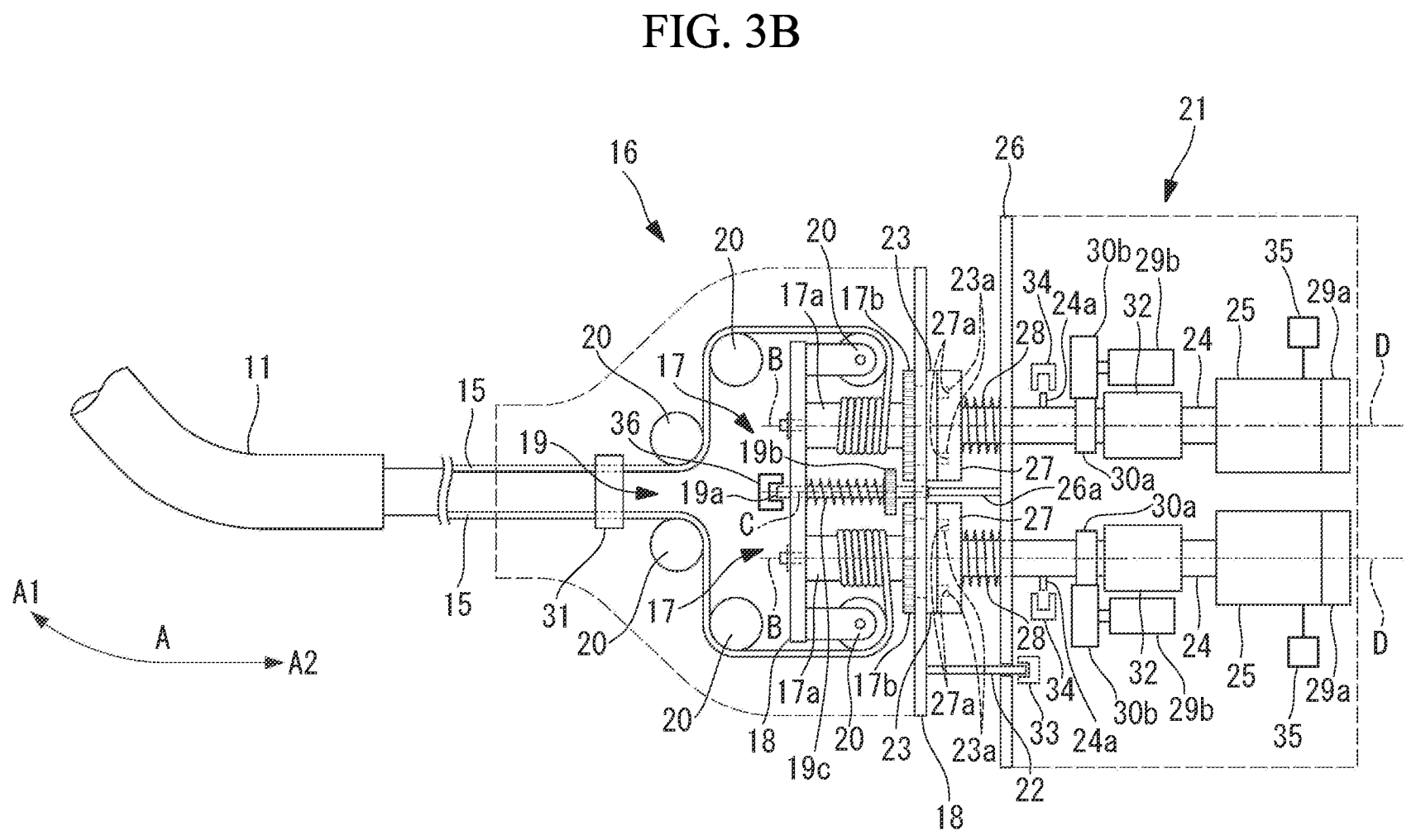

FIGS. 3A and 3B illustrate the configuration of the wire attachment/detachment part 16 and the wire driving part 21. FIG. 3A illustrates the wire attachment/detachment part 16 and the wire driving part 21 in a state of being separated from each other, and FIG. 3B illustrates the wire attachment/detachment part 16 and the wire driving part 21 in a state of being connected to each other. FIGS. 3A and 3B illustrate, for example, the wire driving part 21 and the wire attachment/detachment part 16 including the pair of bending wires 15 for bending the first bending portion 121 vertically. The other wire attachment/detachment parts 16 and the other wire driving parts 21 have the same configuration as that in FIGS. 3A and 3B.

Each wire attachment/detachment part 16 includes a pair of rotary drums 17, a support member 18 supporting the pair of rotary drums 17, and a coupling mechanism 19 coupling the pair of rotary drums 17 to each other.

The support member 18 is a portion fixed to the wire driving part 21 in a state in which the wire attachment/detachment part 16 is coupled to the wire driving part 21.

Each rotary drum 17 is held by the support member 18 so as to be rotatable about a rotation axis B extending in a longitudinal direction A of the insertion part 11. Each rotary drum 17 includes a winding pulley 17*a* disposed coaxially with the rotation axis B and a gear 17*b* fixed to the winding pulley 17*a* and disposed coaxially with the rotation axis B.

The proximal end of each bending wire 15 is guided to the winding pulley 17*a* via a pulley 20 and is wound around the winding pulley 17*a*. As a result of the rotary drum 17 rotating about the rotation axis B, the bending wire 15 is pulled in or fed out. The gear 17*b* is a spur gear that rotates integrally with the winding pulley 17*a*.

In a state in which the wire attachment/detachment part 16 is separated from the wire driving part 21, the coupling mechanism 19 limits rotation of the pair of rotary drums 17 to prevent the pair of bending wires 15 from loosening. The coupling mechanism 19 includes a columnar member 19*a*, a link gear 19*b*, and an elastic member 19*c*.

The columnar member 19*a* is supported by the support member 18 so as to be rotatable about a rotation axis C extending in the longitudinal direction A and movable forward and backward in the longitudinal direction. The rotation axis C is parallel to the rotation axes B of the rotary drums 17. The proximal end of the columnar member 19*a* passes through the support member 18, protrudes to the outside of the wire attachment/detachment part 16, and is exposed on the proximal side of the wire attachment/detachment part 16.

The link gear 19*b* is a spur gear fixed to the columnar member 19*a* and disposed coaxially with the rotation axis C.

The elastic member 19*c* is, for example, a spring, and urges the link gear 19*b* and the columnar member 19*a* toward a proximal side A2.

As illustrated in FIG. 3A, in a state in which the wire attachment/detachment part 16 is separated from the wire driving part 21, the link gear 19*b* and the columnar member 19*a* urged by the elastic member 19*c* are positioned at a first position. The link gear 19*b* at the first position is located between the pair of gears 17*b* to mesh with both of the pair of gears 17*b*. As a result, the pair of rotary drums 17 rotate in mutually opposite directions in conjunction with each other, and the pair of bending wires 15 are pulled in or fed out in conjunction with each other as if a single wire is looped (loop state). In the loop state, when the bending portion 12 is bent upward or downward by an external force, the pair of bending wires 15 do not loosen, and the relationship between the rotation angles of the rotary drums 17 and the bending angle of the bending portion 12 is maintained.

Meanwhile, as illustrated in FIG. 3B, in a state in which the wire attachment/detachment part 16 is connected to the wire driving part 21, the columnar member 19*a* is pressed toward a distal side A1 by an engaging member 26*a* (described below) against the urging force of the elastic member 19*c*, and the link gear 19*b* and the columnar member 19*a* are positioned at the second position. The link gear 19*b* positioned at the second position does not mesh with the pair of gears 17*b*. As a result, the pair of rotary drums 17 do not rotate in conjunction with each other, and the pair of bending wires 15 are pulled in or fed out independently of each other (antagonistic state).

Each wire attachment/detachment part 16 includes dogs 22 provided on the support member 18 to detect attachment/detachment between the wire attachment/detachment part 16 and the wire driving part 21, and coupling parts 23 each provided on the corresponding one of the pair of rotary drums 17 and serving as a mechanism for coupling the bending wire 15 to a motor 25 (described later) of the wire driving part 21.

The dogs 22 are members protruding from the support member 18 to the outside of the wire attachment/detachment part 16 and exposed on the proximal side of the wire attachment/detachment part 16, and are, for example, pin-like members extending parallel to the rotation axes B and C. As illustrated in FIG. 3B, in a state in which the wire attachment/detachment part 16 is connected to the wire driving part 21, the dogs 22 are inserted into the wire driving part 21 through a support member 26.

The coupling parts 23 are disc members fixed to the proximal ends of the winding pulleys 17*a* and disposed coaxially with the rotation axes B, and are exposed on the proximal side of the wire attachment/detachment part 16. Each coupling part 23 has two fitting protrusions 23*a* on the proximal-end surface thereof, on both sides of the rotation axis B.

The wire driving part 21 includes a pair of shafts 24, a pair of motors (power generation units) 25 connected to the pair of shafts 24, and the support member 26 supporting the pair of shafts 24 in a rotatable manner.

Each shaft 24 is supported by the support member 26 so as to be rotatable about a rotation axis D and movable forward and backward in the longitudinal direction A. The rotation axis D is the central axis of the shaft 24 and is aligned with the rotation axis B of the rotary drum 17 in a state in which the attachment/detachment part 13 is connected to the driving device 2.

The motors 25 are, for example, direct-current motors. Each motor 25 generates a rotational force, serving as a driving force, by electric power supplied from the power supply and rotates the corresponding shaft 24 about the rotation axis D. In the wire driving part 21, two encoders, 29*a* and 29*b*, for detecting the rotation speed and the rotation angle of the motor 25 are provided for each motor 25. The first encoder 29*a* is connected to the proximal end of the motor 25. The second encoder 29*b* is connected to the shaft 24 with a pair of gears, 30*a* and 30*b*, meshing with each other.

Figure 4:
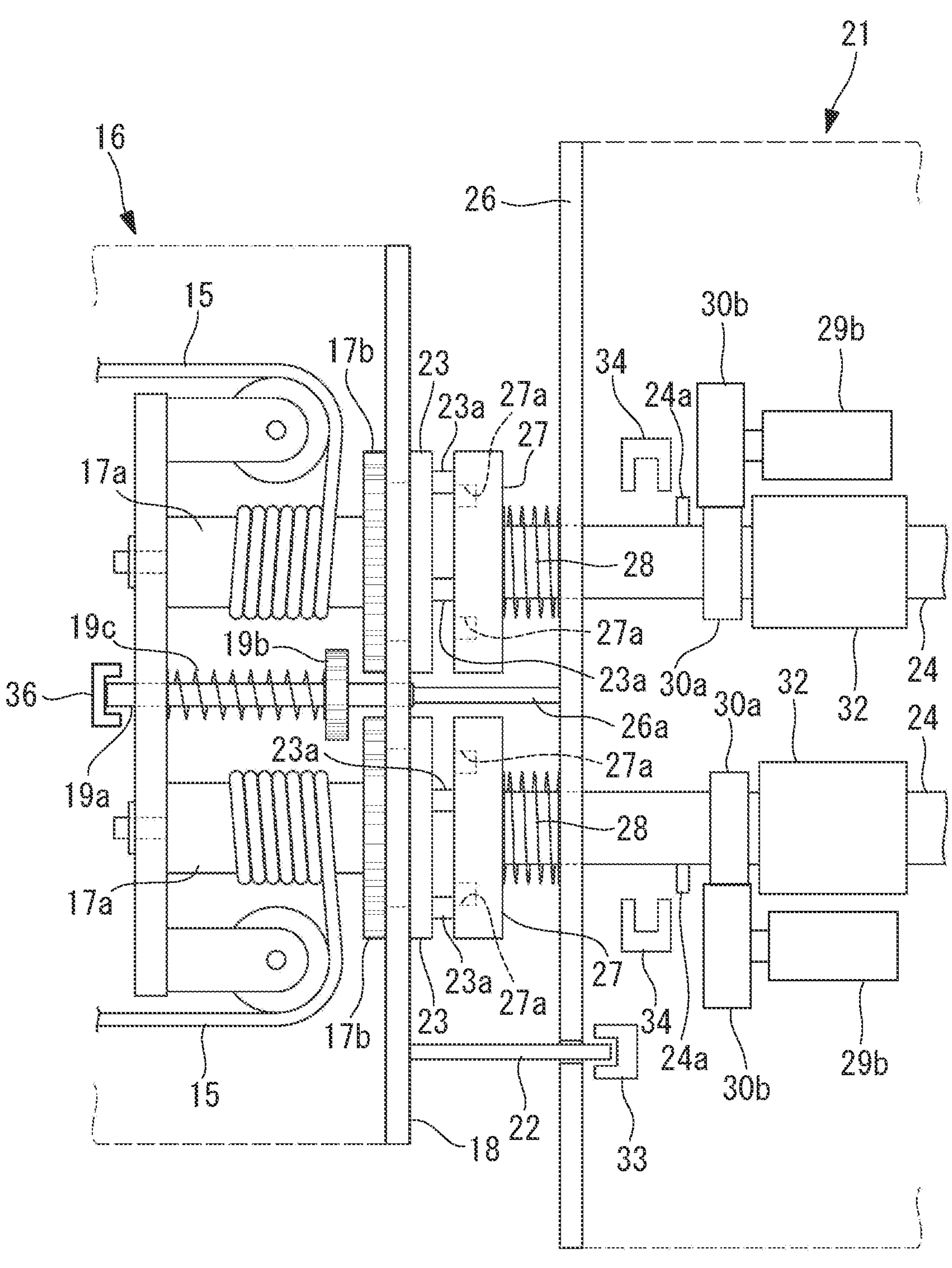
FIG. 4 illustrates another state in which the wire attachment/detachment part is connected to the wire driving part.

The support member 26 has the engaging member 26*a* for decoupling the pair of rotary drums 17 that are coupled to each other by the coupling mechanism 19. The engaging member 26*a* is a columnar member exposed on the distal side of the wire driving part 21 and is provided at a position corresponding to the columnar member 19*a*. As illustrated in FIGS. 3B and 4, in a state in which the wire attachment/detachment part 16 is connected to the wire driving part 21, the engaging member 26*a* presses the columnar member 19*a* to the second position.

Furthermore, the wire driving part 21 includes coupled parts 27 each provided on the corresponding one of the pair of shafts 24 and serving as a mechanism for coupling the motor 25 to the rotary drum 17.

The coupled parts 27 are disc members fixed to the distal ends of the shafts 24 and disposed coaxially with the rotation axes D, and rotate integrally with the shafts 24. The coupled parts 27 are exposed on the distal side of the wire driving part 21. Each coupled part 27 has two fitting recesses 27*a* in the distal-side surface thereof, on both sides of the rotation axis D.

As illustrated in FIGS. 3B and 4, when the fitting protrusions 23*a* and the fitting recesses 27*a* are fitted together, the coupling parts 23 and the coupled parts 27 are coupled together, and thus, the motors 25 are coupled to the bending wires 15 via the rotary drums 17. In this state, the rotary drums 17, the coupling parts 23, the coupled parts 27, and the shafts 24 are integrally rotatable about the rotation axes C and D. Hence, the rotational forces (driving forces) generated by the motors 25 are transmitted, as forces in the longitudinal direction A, to the bending wires 15 via the rotary drums 17.

The manipulator system 100 further includes tension sensors 31, torque sensors 32, attachment/detachment sensors 33, coupling sensors 34, current sensors 35, and antagonistic sensors 36.

The tension sensor 31 and the antagonistic sensor 36 are provided in each of the four wire attachment/detachment parts 16, and the torque sensors 32, the attachment/detachment sensors 33, the coupling sensors 34, and the current sensors 35 are provided in each of the four wire driving parts 21. These sensors 31, 32, 33, 34, 35, and 36 are connected to the control device 4, and the outputs of the sensors 31, 32, 33, 34, 35, and 36 are sequentially transmitted to the control device 4.

The tension sensor 31 is provided for the each of the pair of bending wires 15 to detect the tensions of the bending wires 15.

The torque sensor 32 is provided for each motor 25 to detect the torque of the motor 25. For example, the torque sensor 32 is attached to the shaft 24 to detect the torque about the rotation axis D as the torque of the motor 25.

The attachment/detachment sensors 33 detect attachment/detachment of the wire attachment/detachment part 16 to/from the wire driving part 21. When the wire attachment/detachment part 16 is connected to the wire driving part 21, the attachment/detachment sensors 33 are engaged with the dogs 22 inserted into the wire driving part 21 through the support member 26. The attachment/detachment sensors 33 include, for example, optical sensors that detect contact or proximity with the dogs 22, and detect engagement with the dogs 22 by using the optical sensors. When the dogs 22 are engaged with the attachment/detachment sensors 33, the outputs of the attachment/detachment sensors 33 are ON, whereas when the dogs 22 are not engaged with the attachment/detachment sensors 33, the outputs of the attachment/detachment sensors 33 are OFF.

The attachment/detachment sensors 33 are duplicated. Specifically, each wire attachment/detachment part 16 has two dogs 22, and each wire driving part 21 has two attachment/detachment sensors 33. In FIGS. 3A to 4, only one set of the dog 22 and the attachment/detachment sensor 33 is illustrated.

The coupling sensor 34 is provided for each motor 25. The coupling sensors 34 detect that the motors 25 are coupled to the bending wires 15 by detecting that the coupling parts 23 and the coupled parts 27 are fitted together on the basis of the displacement of the shafts 24. When the coupling parts 23 and the coupled parts 27 are fitted together, the outputs of the coupling sensors 34 are ON, and when the coupling parts 23 and the coupled parts 27 are not fitted together, the outputs of the coupling sensors 34 are OFF.

As illustrated in FIG. 3B, the coupled parts 27 are pressed by the coupling parts 23 and moved to the proximal side A2 together with the shafts 24. The coupling sensors 34 include, for example, optical sensors that detect proximity of dogs 24*a* provided on the shafts 24, and detect fitting between the coupling parts 23 and the coupled parts 27 on the basis of the proximity of the dogs 24*a*.

The coupled parts 27 are urged toward the distal side A1 by elastic members 28, such as compression springs, disposed between the coupled parts 27 and the support member 26. As illustrated in FIG. 3A, in a state in which the wire attachment/detachment part 16 and the wire driving part 21 are separated from each other, the coupled parts 27 have been moved to the distal side A1 together with the shafts 24 by the urging force of the elastic members 28, and the dogs 24*a* are located at positions away from the coupling sensors 34. In this state, the coupling sensors 34 do not detect fitting between the coupling parts 23 and the coupled parts 27.

FIG. 4 illustrates a state in which the attachment/detachment sensors 33 have detected connection between the wire attachment/detachment part 16 and the wire driving part 21, but the coupling parts 23 and the coupled parts 27 are not fitted together due to misalignment between the fitting protrusions 23*a* and the fitting recesses 27*a*. In this state, the coupling sensors 34 do not detect fitting between the coupling parts 23 and the coupled parts 27.

In this case, the control device 4 rotates the motors 25 to rotate the coupled parts 27. When the positions of the fitting recesses 27*a* coincide with the positions of the fitting protrusions 23*a*, the fitting recesses 27*a* and the fitting protrusions 23*a* fit together, the coupled parts 27 are moved to the distal side A1 by the urging force of the elastic members 28, and the coupling sensors 34 detect fitting between the coupling parts 23 and the coupled parts 27.

The current sensor 35 is provided for each motor 25 to detect a current flowing through the motor 25.

The antagonistic sensor 36 is provided for each wire attachment/detachment part 16 to detect an antagonistic state of the pair of bending wires 15. Details of the antagonistic sensor 36 will be described in the fourth embodiment.

Figure 5:
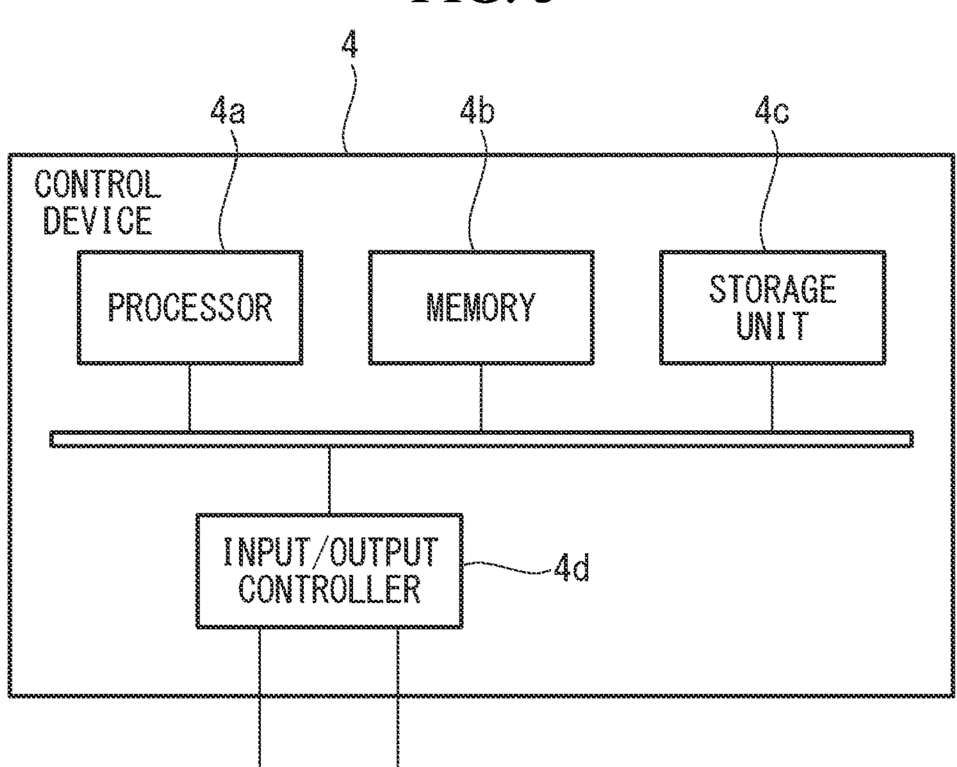
FIG. 5 is a block diagram of a control device for controlling the manipulator system.

The control device 4 is a computer built into the driving device 2 and capable of executing programs. The control device 4 may be a computer disposed outside the driving device 2 and connected to the driving device 2. As illustrated in FIG. 5, the control device 4 includes at least one processor 4*a*, a memory 4*b*, a storage unit 4*c* capable of storing programs and data, and an input/output controller 4*d*.

The storage unit 4*c* is a non-volatile storage medium for storing programs and necessary data and is, for example, a ROM or a hard disk. The functions of the control device 4, which will be described below, are achieved by the programs stored in the storage unit 4*c* being read into the memory 4*b* and executed by the processor 4*a*. At least a part of the functions of the control device 4 may be achieved by a dedicated logic circuit.

Next, a control method for controlling the manipulator system 100 performed by the control device 4 will be described.

Figure 6:
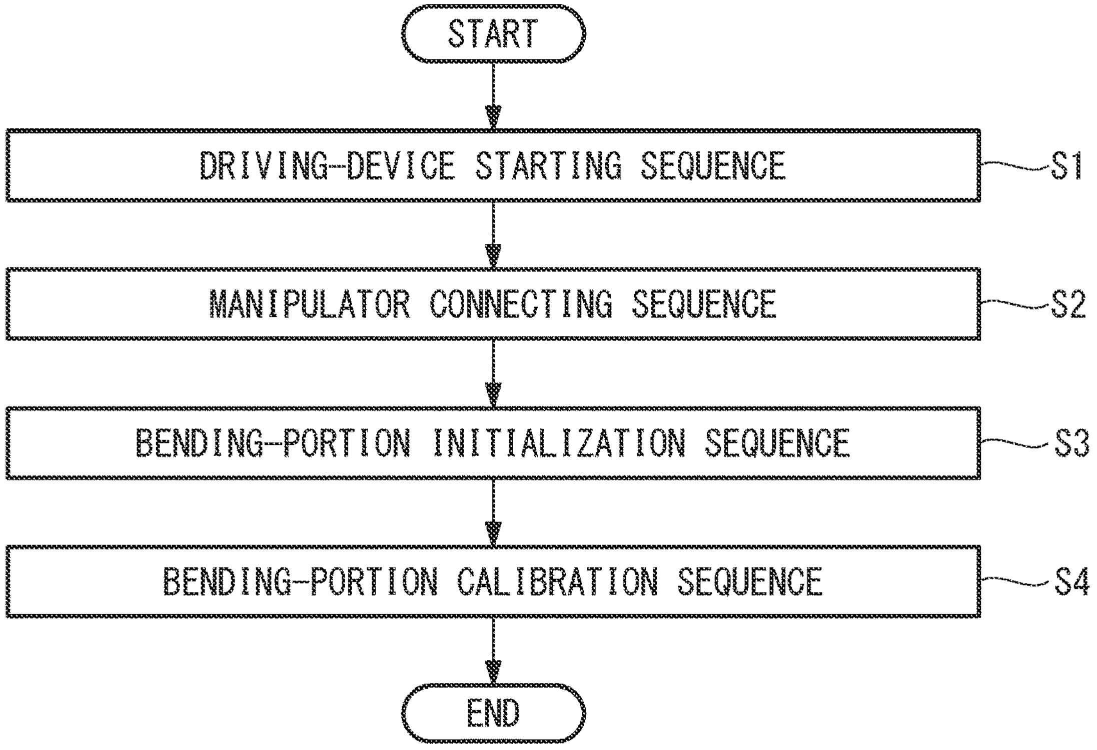
FIG. 6 is a flowchart of a control method performed by the control device at the time of starting the manipulator system.

The control method according to this embodiment is performed to check whether the manipulator 1, the driving device 2, and the control device 4 will operate normally at the time of starting the manipulator system 100. As illustrated in FIG. 6, the control method includes a driving-device starting sequence (first step) S1, a manipulator connecting sequence (second step) S2, a bending-portion initialization sequence (third step) S3, and a bending-portion calibration sequence S4.

After the bending-portion calibration sequence S4, the control device 4 receives an operation input from the operation device 3, and controls the driving device 2 according to the operation input.

FIG. 7 illustrates steps performed in each of the sequences S1, S2, S3, and S4, and the sensors 31, 32, 33, and 34 used in each step.

The driving-device starting sequence S1 is a sequence for starting the driving device 2 and confirming that the driving device 2 operates normally on the basis of the outputs of the encoders 29*a* and 29*b* and the torque sensors (first sensor) 32. The driving-device starting sequence S1 includes step S11 of starting the driving device 2 including the control device 4, and step S12 of performing self-diagnosis of the driving device 2.

In step S12 subsequent to step S11, the control device 4 performs inspections for checking whether the processor 4*a*, the motor 25, and the encoders 29*a* and 29*b*, which are supplied with power, operate normally.

In the inspection of the motor 25, the control device 4 drives the motor 25 and checks the rotation angle of the motor 25, which is the output of the two encoders 29*a* and 29*b*. When the motor 25 and the two encoders 29*a* and 29*b* are all normal, the outputs of the two encoders 29*a* and 29*b* are identical to each other. When the motor 25 is faulty, there is no output from either of the two encoders 29*a* and 29*b*. When one of the encoders 29*a* and 29*b* is faulty, there is no output from only the faulty encoder, or the outputs of the two encoders 29*a* and 29*b* do not match. The control device 4 checks whether the motor 25 and the two encoders 29*a* and 29*b* are normal on the basis of the outputs of the two encoders 29*a* and 29*b*.

In step S12, the control device 4 performs an inspection for checking whether the torque sensor 32 is normal on the basis of the output of the torque sensor 32 and the outputs of the encoders 29*a* and 29*b*.

When the torque sensor 32 is normal, the torque, which is the output of the torque sensor 32, increases with the rotation of the motor 25. The control device 4 rotates the motor 25, confirms that the encoders 29*a* and 29*b* have detected the rotation of the motor 25, and then checks the output of the torque sensor 32. When the output of the torque sensor 32 is higher than or equal to a predetermined value, it is determined that the torque sensor 32 is normal. On the other hand, when the output of the torque sensor 32 is less than the predetermined value despite that the encoders 29*a* and 29*b* have detected the rotation of the motor 25, the control device 4 determines that the torque sensor 32 is abnormal.

The rotational torque of the motor 25 can also be detected from the current flowing through the motor 25. Thus, in step S12, the control device 4 may check whether the torque sensor 32 is normal on the basis of the output of the torque sensor 32 and the output of the current sensor 35.

When it is confirmed that the processor 4*a*, the motor 25, the encoders 29*a* and 29*b*, and the torque sensor 32 are all normal, the control device 4 subsequently performs the manipulator connecting sequence S2. When any abnormality is detected in at least one of the processor 4*a*, the motor 25, the encoders 29*a* and 29*b*, and the torque sensor 32, the control device 4 transitions to an error state and terminates the control method.

The manipulator connecting sequence S2 is a sequence for confirming that the manipulator 1 is connected to the driving device 2 on the basis of the outputs of the attachment/detachment sensors 33 and the coupling sensors (second sensor) 34. The manipulator connecting sequence S2 includes step S21 of confirming that the wire attachment/detachment part 16 of the manipulator 1 is connected to the wire driving part 21 of the driving device 2, step S22 of confirming that the motors 25 are coupled to the bending wires 15, step S23 of inspecting the coupling sensors 34, and step S24 of confirming that the driving force is transmitted from the motors 25 to the bending wires 15.

In step S21, the control device 4 confirms connection between the wire attachment/detachment part 16 and the wire driving part 21 on the basis of the output of the duplicated attachment/detachment sensors 33. Specifically, if the outputs of both the two attachment/detachment sensors 33 are ON, the control device 4 determines that the wire attachment/detachment part 16 and the wire driving part 21 are connected to each other and proceeds to the next step S22. When the output of at least one of the two attachment/detachment sensors 33 is OFF, the control device 4 determines that the attachment/detachment part 13 and the wire driving part 21 are not connected to each other.

In step S22, the control device 4 confirms that the motors 25 are coupled to the bending wires 15 via the coupling parts 23 and the coupled parts 27, which are coupled to each other, on the basis of the outputs of the coupling sensors 34 and the torque sensors 32.

Figure 8A:
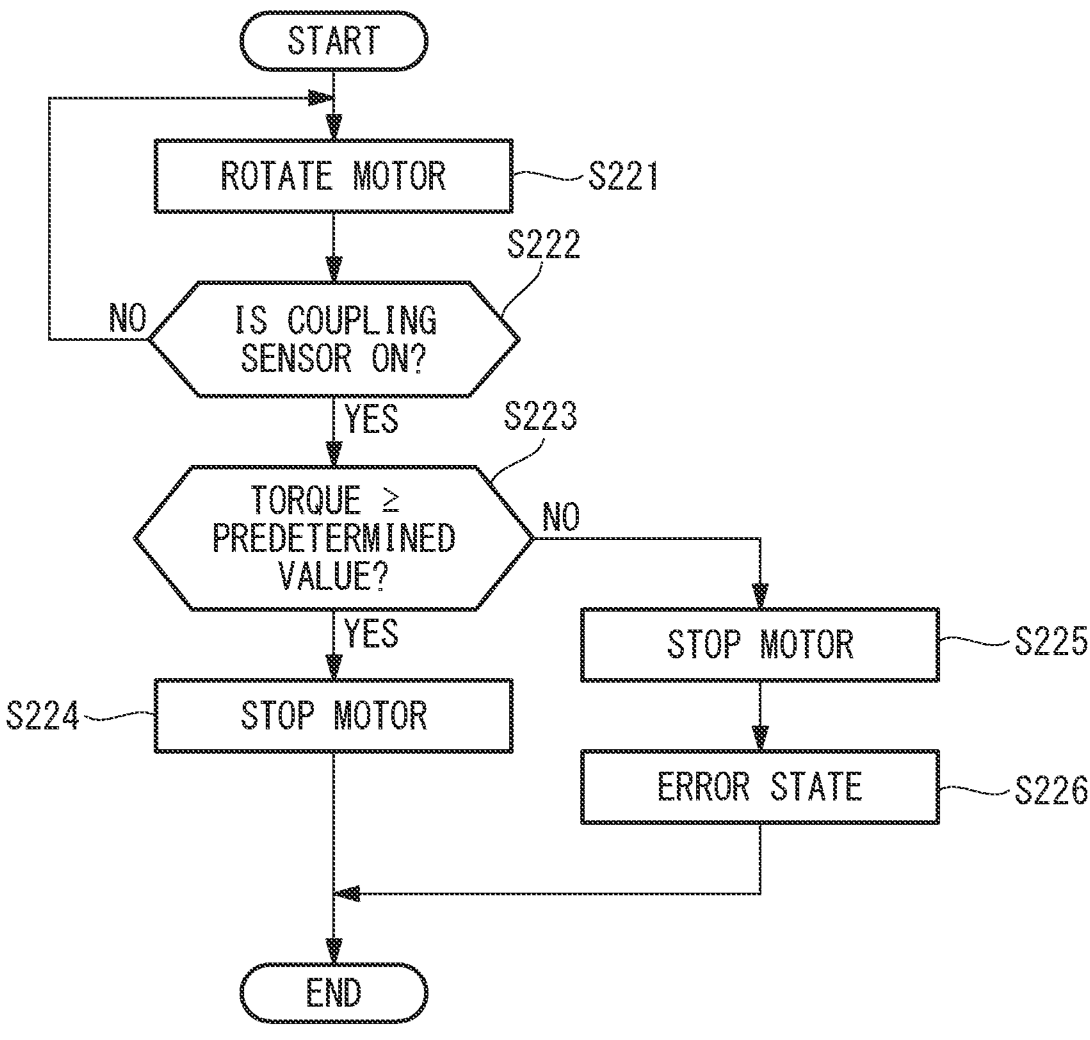
FIG. 8A is a flowchart of a step of checking coupling between a bending wire and a motor.

Specifically, as illustrated in FIG. 8A, the control device 4 rotates the motors 25 (step S221). The rotation of the motors 25 rotates the coupled parts 27, and, when the fitting recesses 27*a* are aligned with the fitting protrusions 23*a*, the coupled parts 27 are coupled to the coupling parts 23, and the outputs of the coupling sensors 34 become ON (YES in step S222).

After confirming that the outputs of the coupling sensors 34 are ON (YES in step S222), the control device 4 subsequently checks the outputs of the torque sensors 32 (step S223). In a state in which the motors 25 are coupled to the bending wires 15 via the coupling parts 23 and the coupled parts 27, which are coupled to each other, the torques of the motors 25 increase due to an increase in the load on the motors 25. If the outputs of the torque sensors 32 are higher than or equal to a predetermined value (YES in step S223), the control device 4 determines that the motors 25 are properly coupled to the bending wires 15, and stops the motors 25 (step S224). If the outputs of the torque sensors 32 are less than the predetermined value (NO in step S223), the control device 4 determines that the motors 25 are not properly coupled to the bending wires 15, stops the motors 25 (step S225), and transitions to an error state (step S226).

In step S223, the control device 4 may check the difference between the outputs of the torque sensors 32 before and after the rotation of the motors 25, instead of the detected torques, which are the outputs of the torque sensors 32. In this case, if the difference is greater than or equal to the predetermined value, it is determined that the motors 25 are properly coupled to the bending wires 15, and if the difference is less than the predetermined value, it is determined that the motors 25 are not properly coupled to the bending wires 15.

The control device 4 performs step S23 in parallel with step S22. In step S23, the control device 4 checks whether the coupling sensors 34 are normal on the basis of the outputs of the coupling sensors 34 and the outputs of the torque sensors that have been confirmed to be normal in sequence S1.

Figure 8B:
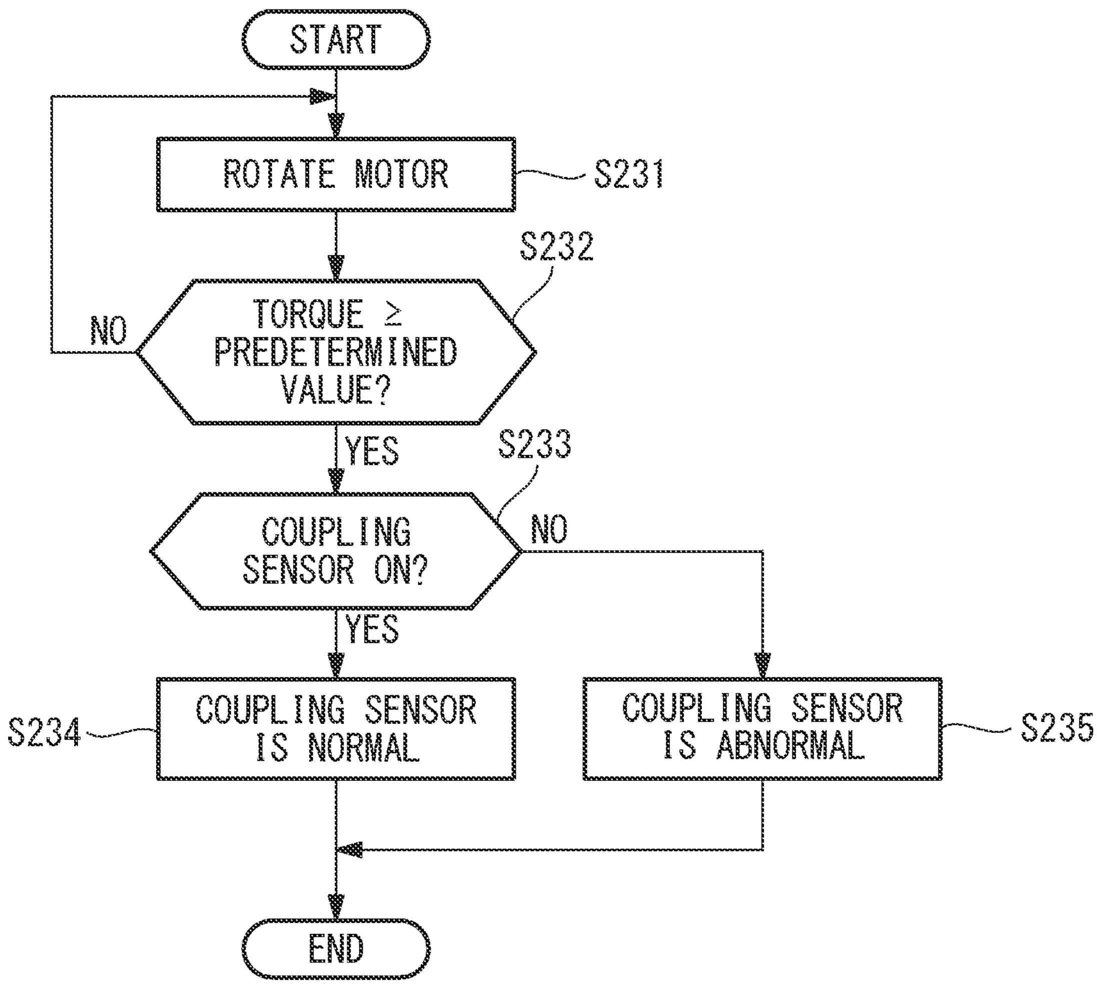
FIG. 8B is a flowchart of a step of inspecting a coupling sensor.

Specifically, as illustrated in FIG. 8B, the control device 4 rotates the motors 25 (step S231), and, after the outputs of the torque sensors 32 have increased to a predetermined value or more (YES in step S232), checks the outputs of the coupling sensors 34 (step S233). If the outputs of the coupling sensors 34 are ON (YES in step S233), the control device 4 determines that the coupling sensors 34 are normal (step S234). When the coupling sensors 34 are OFF, the control device 4 determines that the coupling sensors 34 are abnormal (step S235).

Next, in step S24, the control device 4 inspects a power transmission mechanism in the driving device 2 on the basis of the outputs of the torque sensors 32. The power transmission mechanism is a mechanism for transmitting a driving force from the motors 25 to the coupled parts 27, and includes members, such as the rotation shafts 24, on a driving-force transmission path. The control device 4 rotates the motors 25 and checks the outputs of the torque sensors 32. If the power transmission mechanism is normal, the outputs of the torque sensors 32 change in response to the rotation of the motors 25. If the outputs of the torque sensors 32 change in response to the rotation of the motors 25, the control device 4 determines that the power transmission mechanism is normal. If the outputs of the torque sensors 32 do not change in response to the rotation of the motors 25, the control device 4 determines that the power transmission mechanism is abnormal.

If no abnormality is confirmed in steps S21, S22, S23, and S24, the control device 4 subsequently performs the bending-portion initialization sequence S3. If any abnormality is confirmed in any of steps S21, S22, S23, and S24, the control device 4 transitions to an error state and terminates the control method.

The bending-portion initialization sequence S3 is a sequence for confirming that the bending portion 12 of the manipulator 1 operates normally according to the driving force of the motors 25 on the basis of the outputs of the tension sensors (third sensor) 31, and bringing the bending portion 12 to an initial state before calibration. The bending-portion initialization sequence S3 includes step S31 of initializing the bending angle of the bending portion 12, step S32 of applying initial tensions to the bending wires 15, step S32 of inspecting the tension sensors 31, and step S34 of inspecting a power transmission mechanism in the manipulator 1.

In step S31, the control device 4 straightens the bending portion 12 on the basis of the outputs of the tension sensors 31. For example, the control device 4 rotates the four motors 25 for the first bending portion 121 to make the tensions of the four bending wires 15 for the first bending portion 121 equal to one another, while monitoring the outputs of the tension sensors 31. The control device 4 also rotates the four motors 25 for the second bending portion 122 to make the tensions of the four bending wires 15 for the second bending portion 122 equal to one another while monitoring the outputs of the tension sensors 31.

Next, in step S32, the control device 4 applies a predetermined initial tension to each of the eight bending wires 15 on the basis of the outputs of the tension sensors 31. For example, the control device 4 rotates the motors 25 while monitoring the outputs of the tension sensors 31 and stops the motors 25 at rotation angles at which the tensions detected by the tension sensors 31 are predetermined initial tensions to apply initial tensions to the bending wires 15.

Next, in step S33, the control device 4 checks whether the tension sensors 31 are normal on the basis of the outputs of the tension sensors 31 and the outputs of the torque sensors 32 that have been confirmed to be normal in the sequence S1.

Figure 9:
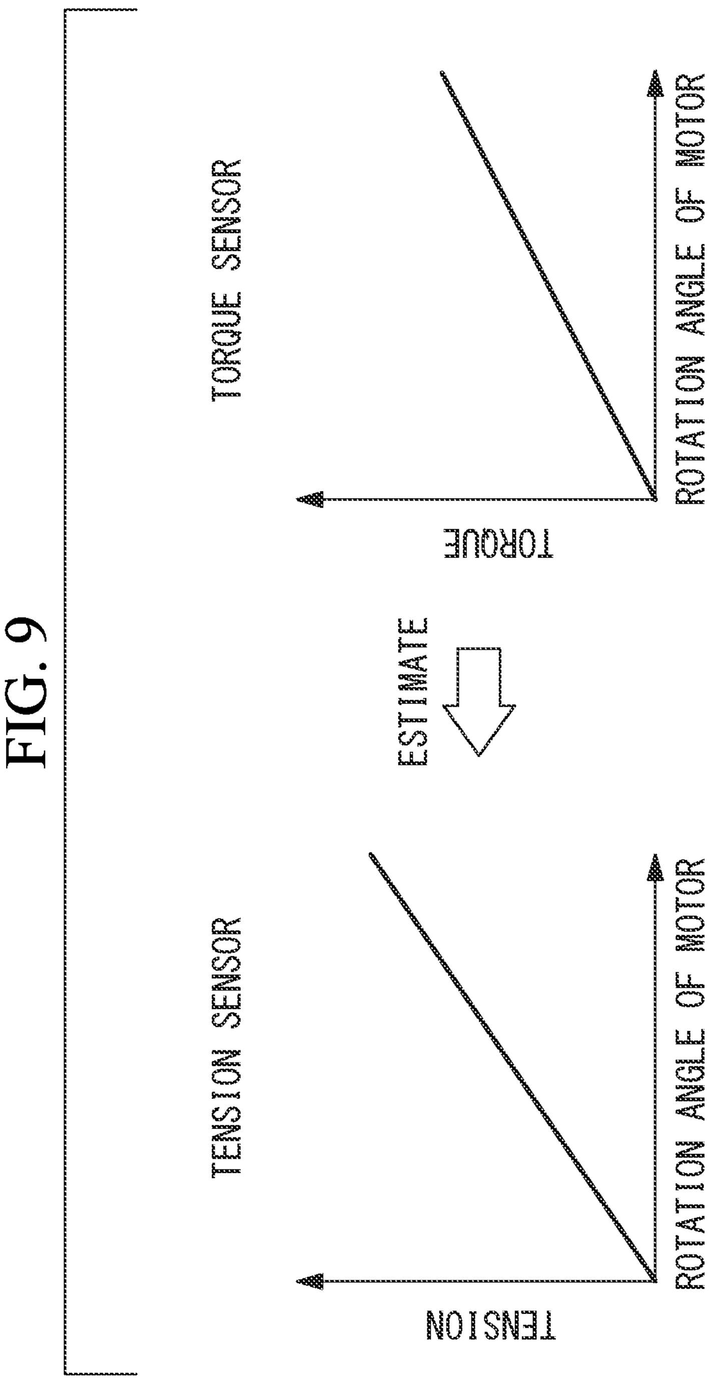
FIG. 9 illustrates the relationship between the tension of the bending wire, detected by the tension sensor, and the torque of the motor, detected by a torque sensor.

FIG. 9 illustrates the relationship between the outputs of the tension sensors 31 and the outputs of the torque sensors 32. As illustrated in FIG. 9, when the tension sensors 31 are normal, there is a predetermined correlation between the torques, which are the outputs of the torque sensors 32, and the tensions, which are the outputs of the tension sensors 31, and the tensions increase as the torques increases. Hence, the outputs of the tension sensors 31 can be estimated from the outputs of the torque sensors 32.

Figure 8C:
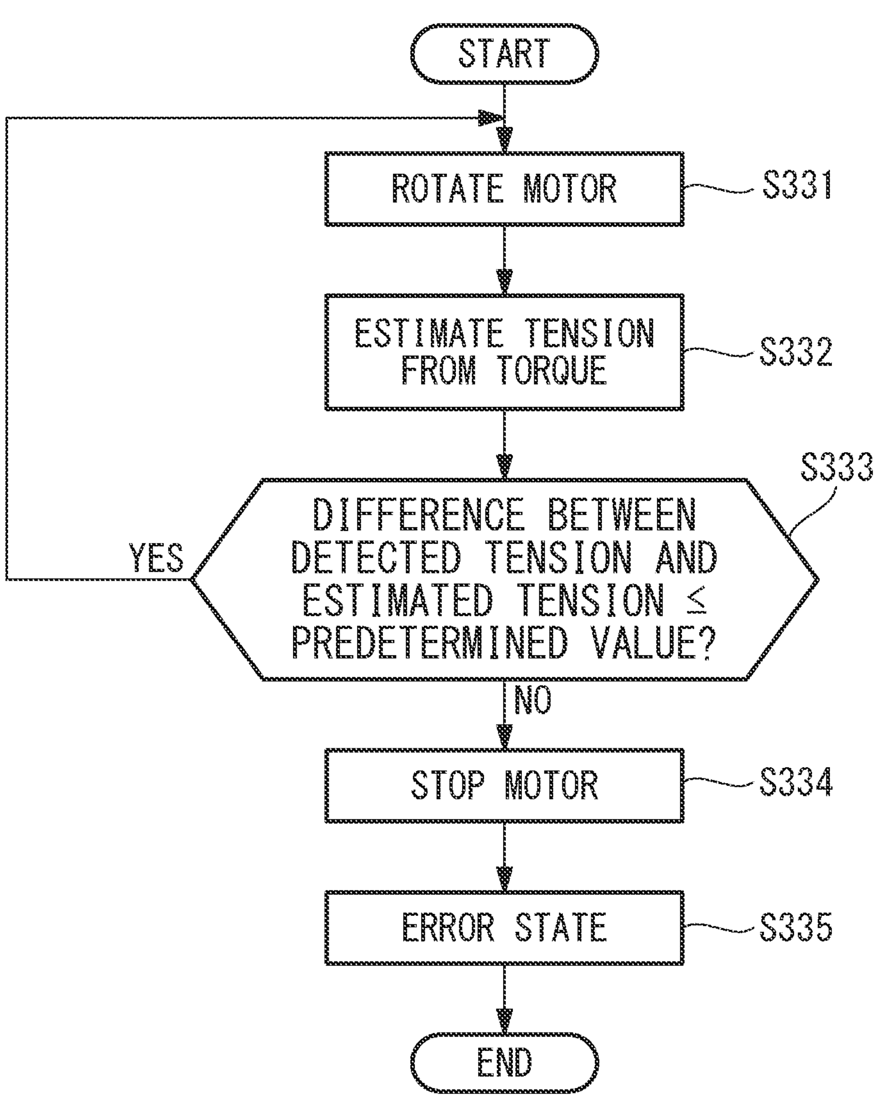
FIG. 8C is a flowchart of a step of inspecting a tension sensor.

As illustrated in FIG. 8C, the control device 4 rotates the motors 25 (step S331), and then calculates estimated tensions of the bending wires 15 from the torques of the motors 25, which are the outputs of the torque sensors 32 (step S332). Next, the control device 4 calculates the difference between the detected tensions, which are the outputs of the tension sensors 31, and the estimated tensions. If the magnitude of the difference is less than or equal to a predetermined value (YES in step S333), the control device 4 determines that the tension sensors 31 are normal and proceeds to the next step S34. While the motors 25 are rotated, the control device 4 repeats steps S331 to S333 to constantly perform inspection of the tension sensors 31.

If the difference is larger than the predetermined value (NO in step S333), the control device 4 determines that the tension sensors 31 are abnormal, stops the motors 25 (step S334), and transitions to an error state (step S335).

In steps S331 and S332, the control device 4 may calculate estimated torques of the motors 25 from the detected tensions of the bending wires 15, which are the outputs of the tension sensors 31, and calculate the difference between the detected torques, which are the outputs of the torque sensors 32, and the estimated torques.

In step S34, the control device 4 inspects the power transmission mechanism in the manipulator 1 on the basis of the outputs of the tension sensors 31. The power transmission mechanism is a mechanism for transmitting a driving force from the coupling parts 23 to the bending portion 12, and includes members, such as the coupling parts 23, the rotary drums 17, and the bending wires 15, on the driving-force transmission path. The control device 4 rotates the motors 25 and checks the outputs of the tension sensors 31. If the power transmission mechanism is normal, the outputs of the tension sensors 31 change in response to the rotation of the motors 25. If the outputs of the tension sensors 31 change in response to the rotation of the motors 25, the control device 4 determines that the power transmission mechanism is normal. If the outputs of the tension sensors 31 do not change in response to the rotation of the motors 25, the control device 4 determines that the power transmission mechanism is abnormal.

If no abnormality is confirmed in steps S31, S32, S33, and S34, the control device 4 subsequently performs the bending-portion calibration sequence S4. If any abnormality is confirmed in any of steps S31, S32, S33, and S34, the control device 4 transitions to an error state and terminates the control method.

The bending-portion calibration sequence S4 is a sequence for calibrating the relationship between the amounts of rotation of the motors 25 and the bending angle of the bending portion 12. In order to accurately control the bending angle of the bending portion 12 by means of rotation of the motors 25, the amounts of rotation of the motors 25 and the bending angle of the bending portion 12 need to have a predetermined relationship. However, the relationship between the amounts of rotation of the motors 25 and the bending angle of the bending portion 12 may change for some reason. In the sequence S4, the control device 4 rotates the motors 25 to adjust the relationship between the amounts of rotation of the motors 25 and the bending angle of the bending portion 12 on the basis of the rotation angles of the motors 25 detected by the encoders 29*a* and 29*b* and the bending angle of the bending portion 12 acquired from an endoscopic image.

After completion of the sequence S4, the manipulator system 100 is ready to be operated by the operation device 3.

When connecting the manipulator 1 to the driving device 2, an operator, such as a nurse, moves while holding the insertion part 11 and the attachment/detachment parts 13 and 14 with hands and performs a connecting task. Hence, to enable the operator to easily prepare the manipulator 1 himself or herself, it is important to reduce the weight and size of the insertion part 11 and the attachment/detachment parts 13 and 14. The driving device 2 is also desired to be small so that the user can install the driving device 2 anywhere.

The manipulator system 100 having the electrically actuated and detachable manipulator 1 has a number of sensors. For example, the manipulator 1 having the two-stage bending portions 121 and 122 has the tension sensors 31, the torque sensors 32, and the coupling sensors 34 corresponding to the eight bending wires 15. Because these sensors 31, 32, and 34 are expensive, reducing the number of sensors is important to reduce the product cost of the manipulator system 100.

According to this embodiment, in the inspection of the coupling sensors 34 in step S23, it is checked whether the coupling sensors 34 are normal on the basis of the outputs of the coupling sensors 34 and the outputs of the torque sensors 32. If both the torque sensors 32 and the coupling sensors 34 are normal, the outputs of the torque sensors 32 and the outputs of the coupling sensors 34 correlate with each other. Thus, by combining the coupling sensors 34 with the torque sensors 32 that have been confirmed to be normal, it is possible to detect an abnormality of the coupling sensors 34 without duplicating the coupling sensors 34. Thus, it is possible to reduce the number of coupling sensors 34 provided in the driving device 2.

Furthermore, in the confirmation of coupling in step S22, coupling between the bending wires 15 and the motors 25 can be doubly confirmed on the basis of the outputs of the coupling sensors 34 and the torque sensors 32.

Furthermore, according to this embodiment, in the inspection of the tension sensors 31 in step S33, it is checked whether the tension sensors 31 are normal on the basis of the outputs of the tension sensors 31 and the outputs of the torque sensors 32. If both the torque sensors 32 and the tension sensors 31 are normal, the outputs of the torque sensors 32 and the outputs of the tension sensors 31 correlate with each other. Thus, by combining the tension sensors 31 with the torque sensors 32 that have been confirmed to be normal, it is possible to detect an abnormality of the tension sensors 31 without duplicating the tension sensors 31. Thus, it is possible to reduce the number of the tension sensors 31 provided in the manipulator 1. Thus, it is possible to reduce the size and weight of the attachment/detachment part 13.

Second Embodiment

Next, a manipulator system control method, a manipulator system control device, and a manipulator system according to a second embodiment of the present invention will be described with reference to the drawings.

In this embodiment, configurations different from those in the first embodiment will be described, and configurations common to those in the first embodiment will be denoted by the same reference signs, and the descriptions thereof will be omitted.

As in the first embodiment, the manipulator system 100 according to this embodiment includes the manipulator 1, the driving device 2, the control device 4, the operation device 3, the image processor 5, and the display device 6.

FIG. 10 illustrates steps performed in each of the sequences S1, S2, S3, and S4 of the control method according to this embodiment, and the sensors 31, 32, 33, and 34 used in each step. As illustrated in FIG. 10, the control method according to this embodiment differs from that according to the first embodiment in the manipulator connecting sequence S2.

The manipulator connecting sequence S2 in this embodiment includes step S21, step S25 of inspecting the tension sensors 31, step S22' of confirming that the motors 25 are coupled to the bending wires 15, and step S24.

In step S25, the control device 4 checks whether the tension sensors 31 are normal on the basis of the outputs of the tension sensors 31 and the outputs of the torque sensors 32 that have been confirmed to be normal in the sequence S1. Specifically, similarly to step S33 in the first embodiment, the control device 4 rotates the motors 25, calculates estimated tensions of the bending wires 15 from the torques of the motors 25, and calculates the difference between the detected tensions and the estimated tensions. If the difference is less than or equal to a predetermined value, the control device 4 determines that the tension sensors 31 are normal and proceeds to the next step S22'. If the magnitude of the difference is larger than the predetermined value, the control device 4 determines that the tension sensors 31 are abnormal, stops the motors 25, and transitions to an error state.

In step S25, the control device 4 may calculate estimated torques of the motors 25 from the detected tensions of the bending wires 15, which are the outputs of the tension sensors 31, and calculate the difference between the detected torques, which are the outputs of the torque sensors 32, and the estimated torque.

In step S22', the control device 4 confirms that the motors 25 are coupled to the bending wires 15 via the coupling parts 23 and the coupled parts 27, which are coupled to each other, on the basis of the outputs of the tension sensors 31 and the torque sensors 32.

Figure 11:
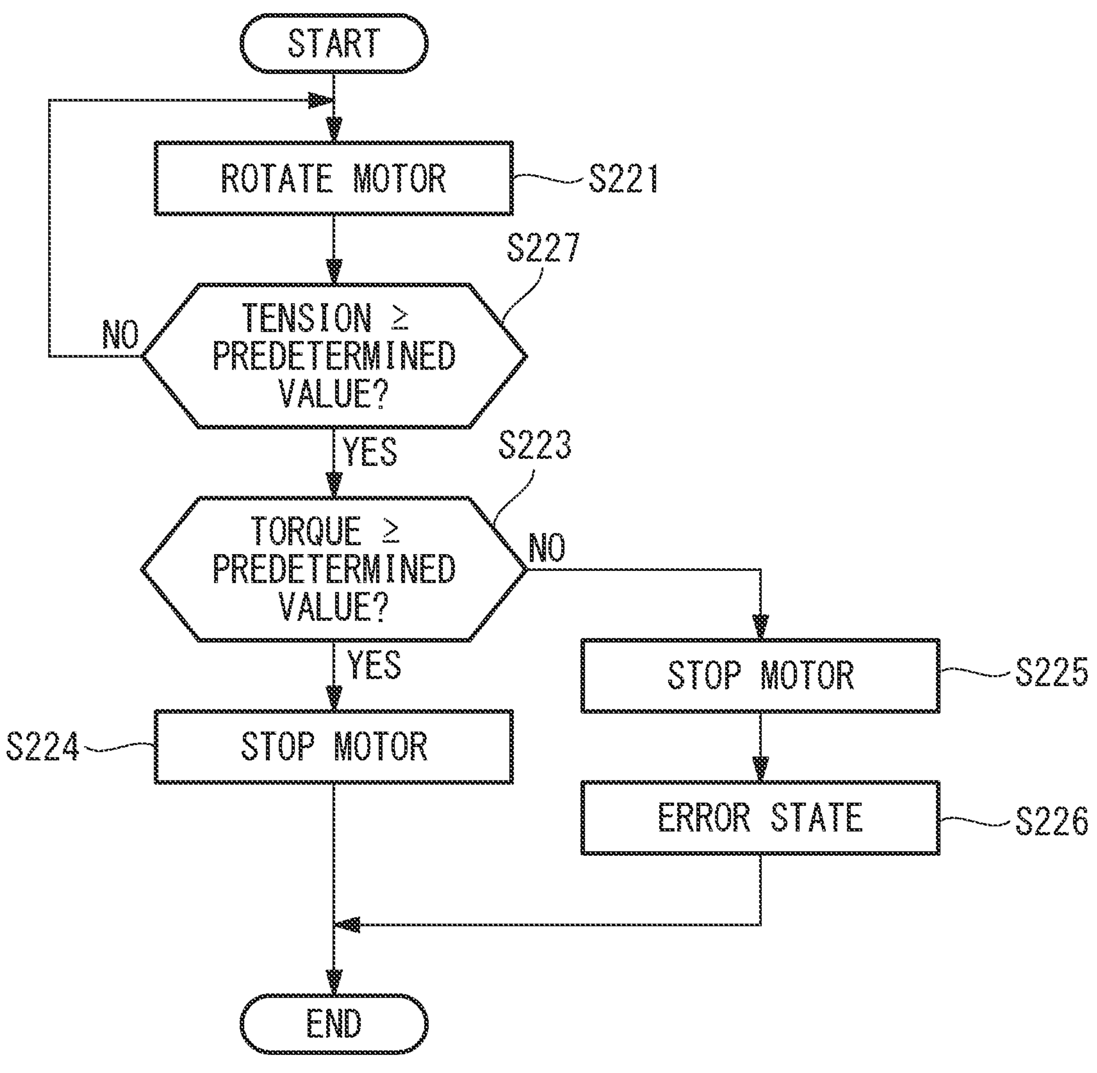
FIG. 11 is a flowchart of a step of checking coupling between the bending wire and the motor.

Specifically, as illustrated in FIG. 11, the control device 4 rotates the motors 25 (step S221). The rotation of the motors 25 rotates the coupled parts 27, and, when the fitting recesses **27*a* are aligned with the fitting protrusions 23*a*, the coupled parts 27 are coupled to the coupling parts 23, increasing the tensions of the bending wires 15**.

After confirming that the tensions of the bending wires 15 have increased to a predetermined value or more (YES in step S227), the control device 4 subsequently checks the outputs of the torque sensors 32. In a state in which the motors 25 are coupled to the bending wires 15, the torques of the motors 25 increase due to the tensions of the bending wires 15. If the outputs of the torque sensors 32 are higher than or equal to a predetermined value (YES in step S223), the control device 4 determines that the motors 25 are properly coupled to the bending wires 15, and stops the motors 25 (step S224). If the outputs of the torque sensors 32 are less than the predetermined value (NO in step S223), the control device 4 determines that the motors 25 are not properly coupled to the bending wires 15, stops the motors 25 (step S225), and transitions to an error state (step S226).

As described above, according to this embodiment, in the inspection of the tension sensors 31 in step S25, it is checked whether the tension sensors 31 are normal on the basis of the outputs of the tension sensors 31 and the outputs of the torque sensors 32. As described above, by combining the tension sensors 31 with the torque sensors 32 that have been confirmed to be normal, it is possible to detect an abnormality of the tension sensors 31 without duplicating the tension sensors 31. Thus, it is possible to reduce the number of the tension sensors 31 provided in the manipulator 1.

Furthermore, according to this embodiment, in step S22', coupling between the bending wires 15 and the motors 25 is doubly confirmed on the basis of the outputs of the tension sensors 31 and the torque sensors 32. This makes it possible to omit the coupling sensors 34 and thus to further reduce the number of sensors provided in the driving device 2 compared with that in the first embodiment.

Third Embodiment

Next, a manipulator system control method, a manipulator system control device, and a manipulator system according to a third embodiment of the present invention will be described with reference to the drawings.

In this embodiment, configurations different from those in the first embodiment will be described, and configurations common to those in the first embodiment will be denoted by the same reference signs, and the description thereof will be omitted.

As in the first embodiment, the manipulator system 100 according to this embodiment includes the manipulator 1, the driving device 2, the control device 4, the operation device 3, the image processor 5, and the display device 6.

FIG. 12 illustrates steps performed in each of the sequences S1, S2, S3, and S4 of the control method according to this embodiment, and the sensors 31, 32, 33, 34, and 35 used in each step. As illustrated in FIG. 12, the control method according to this embodiment differs from that according to the first embodiment in the manipulator connecting sequence S2 and the bending-portion initialization sequence S3.

The manipulator connecting sequence S2 in this embodiment includes step S21, step S26 of inspecting the torque sensors 32, step S22" of confirming that the motors 25 are coupled to the bending wires 15, and step S24.

In step S26, the control device 4 checks whether the torque sensors 32 are normal on the basis of the outputs of the torque sensors 32 and the output of the current sensors (fourth sensor) 35.

Figure 13:
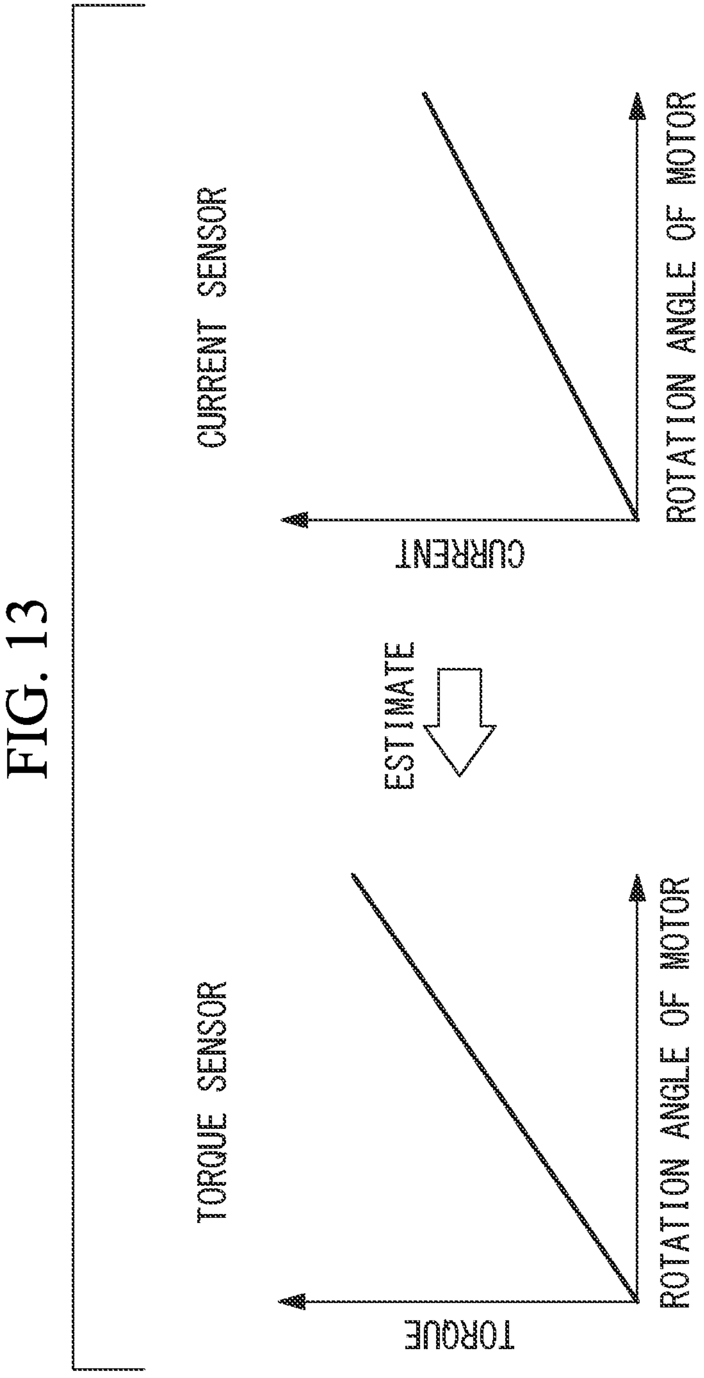
FIG. 13 illustrates the relationship between the torque of the motor, detected by a torque sensor, and the current in the motor, detected by a current sensor.

FIG. 13 illustrates the relationship between the outputs of the torque sensors 32 and the outputs of the current sensors 35. As illustrated in FIG. 13, when the torque sensors 32 are normal, there is a predetermined correlation between the magnitudes of the torques, which are the outputs of the torque sensors 32, and the magnitudes of the currents of the motors 25, which are the outputs of the current sensors 35, and the torques increase as the currents increase. Hence, the outputs of the torque sensors 32 can be estimated from the outputs of the current sensors 35.

For example, the control device 4 rotates the motors 25, and calculates estimated torques of the motors 25 from the currents of the motors 25 detected by the current sensors 35. Next, the control device 4 calculates the difference between the detected torques, which are the outputs of the torque sensors 32, and the estimated torques. If the magnitude of the difference is less than or equal to a predetermined value, the control device 4 determines that the torque sensors 32 are normal, and if the magnitude of the difference is larger than the predetermined value, the control device 4 determines that the torque sensors 32 are abnormal.

Next, in step S22", the control device 4 confirms that the motors 25 are coupled to the bending wires 15 via the coupling parts 23 and the coupled parts 27, which are coupled to each other, on the basis of the outputs of the torque sensors 32 and the outputs of the current sensors 35.

Figure 14:
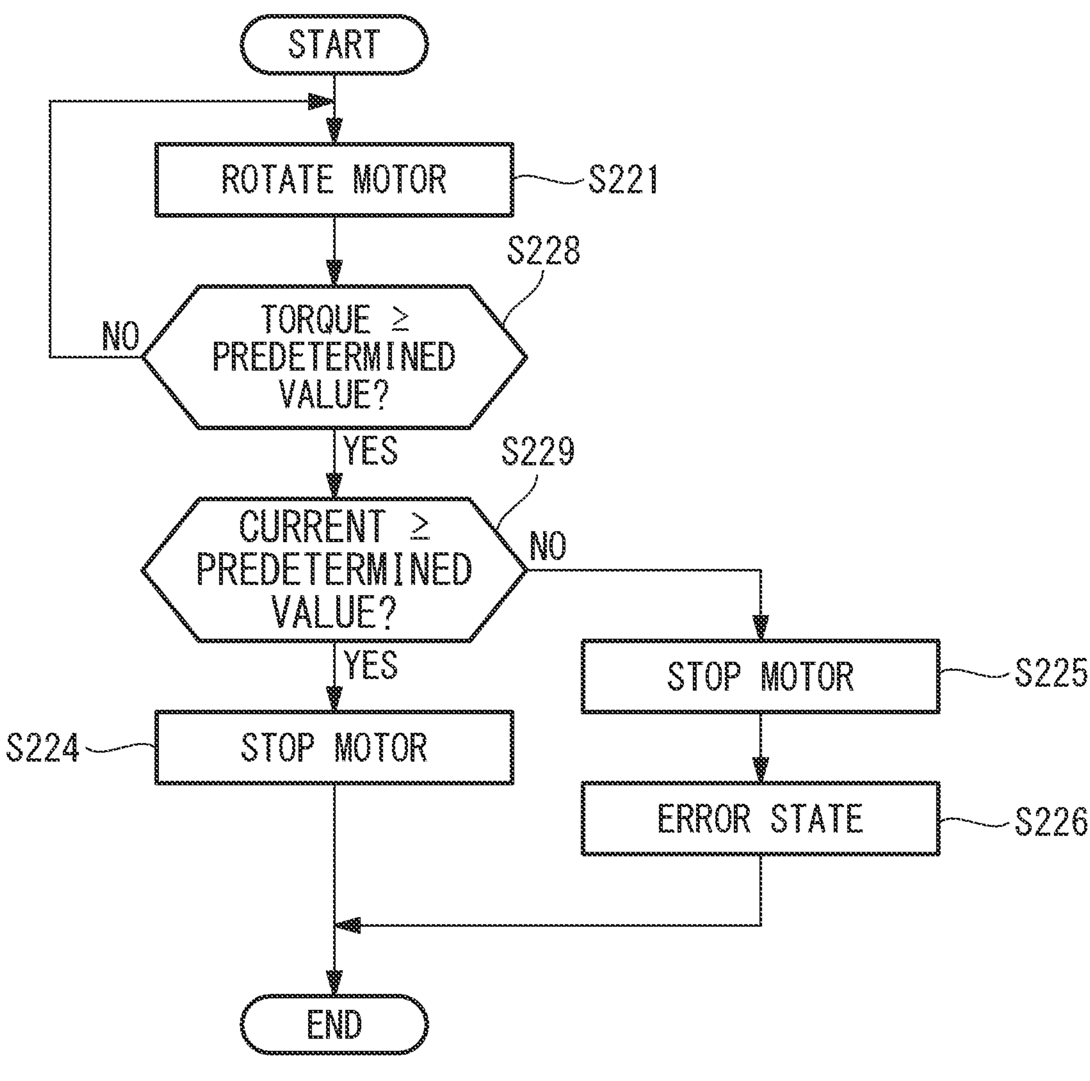
FIG. 14 is a flowchart of a step of checking coupling between the bending wire and the motor.

Specifically, as illustrated in FIG. 14, the control device 4 rotates the motors 25 (step S221). The rotation of the motors 25 rotates the coupled parts 27, and, when the fitting recesses 27*a* are aligned with the fitting protrusions 23*a*, the coupled parts 27 are coupled to the coupling parts 23, increasing the torques of the motors 25.

After confirming that the torques of the motors 25 have increased to a predetermined value or more (YES in step S228), the control device 4 subsequently checks the outputs of the current sensors 35. In a state in which the motors 25 are coupled to the bending wires 15, the currents of the motors 25 increase due to an increase in the load on the motors 25. If the outputs of the current sensors 35 are higher than or equal to a predetermined value (YES in step S229), the control device 4 determines that the motors 25 are properly coupled to the bending wires 15 and stops the motors 25 (step S224). If the outputs of the current sensors 35 are less than the predetermined value (NO in step S229), the control device 4 determines that the motors 25 are not properly coupled to the bending wires 15, stops the motors 25 (step S225), and transitions to an error state (step S226).

The bending-portion initialization sequence S3 in this embodiment includes step S31, step S32, step S35 of inspecting the torque sensors 32, and step S34 of inspecting the power transmission mechanism in the manipulator 1.

In step S35, similarly to step S26, the control device 4 checks whether the torque sensors 32 are normal on the basis of the outputs of the torque sensors 32 and the outputs of the current sensors 35.

As described above, according to this embodiment, in the inspection of the torque sensors 32 in step S26, it is checked whether the torque sensors 32 are normal on the basis of the outputs of the torque sensors 32 and the outputs of the current sensors 35. The outputs of the torque sensors 32 and the outputs of the current sensors 35 correlate with each other. Hence, by combining the torque sensors 32 and the current sensors 35, it is possible to detect an abnormality of the torque sensors 32 without duplicating the torque sensors 32.

Furthermore, in step S22", coupling between the bending wires 15 and the motors 25 is doubly confirmed on the basis of the outputs of the torque sensors 32 and the outputs of the current sensors 35. This makes it possible to omit the coupling sensors 34 and thus to further reduce the number of sensors provided in the driving device 2 compared with that in the first embodiment.

Fourth Embodiment

Next, a manipulator system control method, a manipulator system control device, and a manipulator system according to a fourth embodiment of the present invention will be described with reference to the drawings.

In this embodiment, configurations different from those in the first embodiment will be described, and configurations common to those in the first embodiment will be denoted by the same reference signs, and the description thereof will be omitted.

As in the first embodiment, the manipulator system 100 according to this embodiment includes the manipulator 1, the driving device 2, the control device 4, the operation device 3, the image processor 5, and the display device 6.

FIG. 15 illustrates steps performed in each of sequences S1, S2, S3, and S4 of the control method according to this embodiment, and the sensors 31, 32, 33, 34, and 36 used in each step. As illustrated in FIG. 15, the control method according to this embodiment differs from that according to the first embodiment in the manipulator connecting sequence S2.

The manipulator connecting sequence S2 in this embodiment includes step S21' of confirming that the wire attachment/detachment part 16 of the manipulator 1 is connected to the wire driving part 21 of the driving device 2, step S22, step 23, and step S24.

In step S21', the control device 4 confirms connection between the wire attachment/detachment part 16 and the wire driving part 21 on the basis of the outputs of the attachment/detachment sensors (fifth sensor) 33 and the outputs of the antagonistic sensors (sixth sensor) 36.

Each antagonistic sensor 36 detects an antagonistic state of a pair of bending wires 15. When the pair of bending wires 15 are in an antagonistic state, the columnar member 19*a* and the gear 19*b* of the coupling mechanism 19 are positioned at the second position. For example, the antagonistic sensor 36 includes an optical sensor that detects contact or proximity with the columnar member 19*a*, and detects the antagonistic state by detecting that the columnar member 19*a* is positioned at the second position with the optical sensor.

Figure 16:
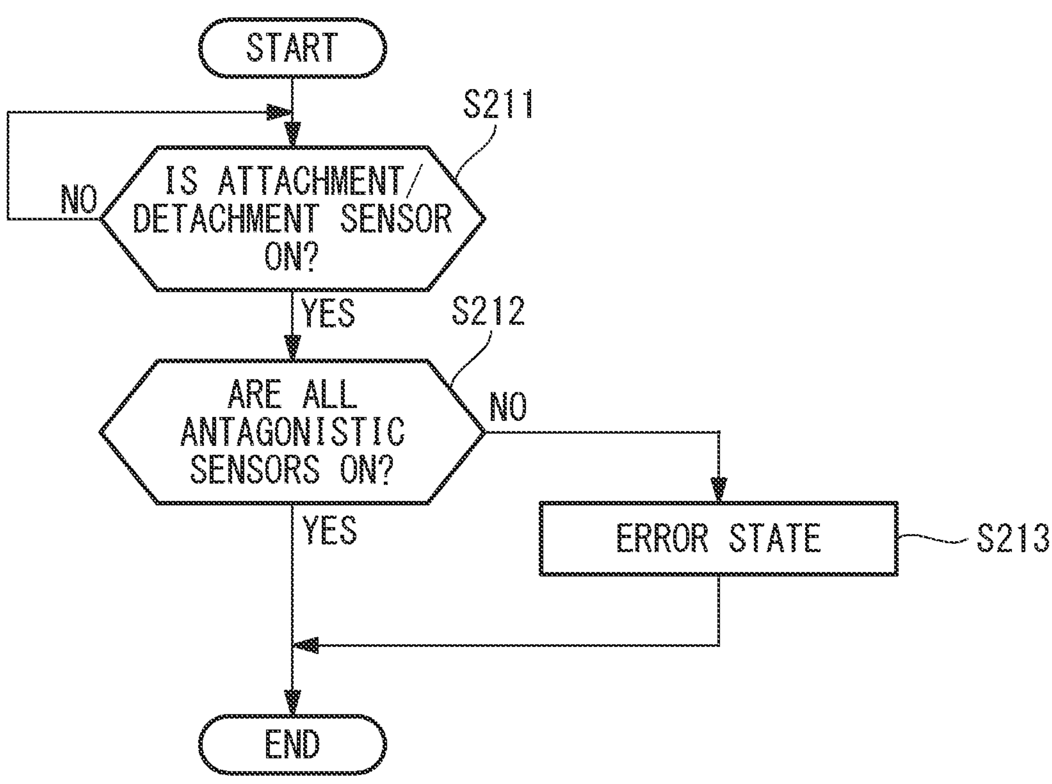
FIG. 16 is a flowchart of a step of checking connection between a wire attachment/detachment part and a wire driving part.

As illustrated in FIG. 16, in step S21', the control device 4 confirms that the attachment/detachment sensors 33 are ON (YES in step S211), and then checks the outputs of the antagonistic sensors 36 (step S212). If the outputs of all the antagonistic sensors 36 of the four wire attachment/detachment parts 16 are ON, the control device 4 determines that the wire attachment/detachment parts 16 and the wire driving parts 21 are connected to each other. If the output of at least one of the antagonistic sensors 36 is OFF, the control device 4 determines that the wire attachment/detachment parts 16 and the wire driving parts 21 are not connected to each other, and transitions to an error state (step S213).

As described above, according to this embodiment, in step S21', connection between the wire attachment/detachment parts 16 and the wire driving parts 21 is doubly confirmed on the basis of the outputs of the attachment/detachment sensors 33 and the outputs of the antagonistic sensors 36. This makes it possible to reliably and accurately detect whether the wire attachment/detachment parts 16 and the wire driving parts 21 are connected to each other without duplicating the attachment/detachment sensors 33, and thus to reduce the number of attachment/detachment sensors 33 provided in the driving device 2 compared with that in the first embodiment.

Step S21' in this embodiment may be applied to the second and third embodiments. Specifically, step S21' may be performed instead of step S21 in the second and third embodiments.

In the above-described embodiments, the sensor in which an abnormality has been detected in sequence S1, S2, or S3 may be notified to an operator. This configuration enables the operator, upon being notified of the sensor in which an abnormality has been detected, to appropriately determine which of the manipulator and the driving device is to be replaced.

For example, in the first embodiment, if an abnormality of the torque sensors 32 is detected in the inspection in step S12, the abnormality of the torque sensors 32 is notified. If an abnormality of the coupling sensors 34 is detected in the inspection in step S23, the abnormality of the coupling sensors 34 is notified. If an abnormality of the tension sensors 31 is detected in the inspection in step S33, the abnormality of the tension sensors 31 is notified.

The operator replaces the driving device with another driving device if an abnormality of the torque sensors 32 or the coupling sensors 34 is detected, and replaces the manipulator with another manipulator if an abnormality of the tension sensors 31 is detected.

Although the manipulator 1 has been described as an electrically actuated flexible endoscope in the above-described embodiments, the manipulator 1 is not limited thereto and may be another device that has an electrically driven movable portion. For example, the manipulator may be a rigid endoscope including the bending portion 12, or may be a surgical treatment instrument including a movable portion that performs a desired operation, such as opening/closing or advancing/retracting, according to the driving force transmitted from the motors through the driving wires.

In the above-described embodiments, the inspections performed in steps S1, S2, S3, and S4 may be performed not only at the time of starting, but also at any timing after operation by the operation device 3 becomes possible.

Although it has been described that the power generation units include the motors 25 in the above-described embodiments, the power generation units may be in other forms as long as the power generation units can generate a driving force for moving the movable portion. For example, the power generation units may include actuators that generate a linear force as the driving force. The design of the power transmission mechanism between the power generation units and the bending wires 15 may be changed according to the form of the power generation unit.

REFERENCE SIGNS LIST

1 Manipulator, endoscope
2 Driving device
4 Control device
12, 121, 122 Bending portion (movable portion)
16 Wire attachment/detachment part
21 Wire driving part
25 Motor (power generation unit)
31 Tension sensor (second sensor, third sensor)
32 Torque sensor (first sensor)
33 Attachment/detachment sensor (fifth sensor)
34 Coupling sensor (second sensor)
35 Current sensor (fourth sensor)
36 Antagonistic sensor (sixth sensor)
S1 Driving-device starting sequence (first step)
S2 Manipulator connecting sequence (second step)
S3 Bending-portion initialization sequence (third step)

The invention claimed is:

1. A manipulator system comprising:

a manipulator;

a driving device comprising at least one actuator, the manipulator is detachably connected to the driving device and the driving device electrically drives the manipulator;

a controller comprising hardware, the controller being configured to control the manipulator and the driving device;

a first sensor provided in the driving device; and a second sensor provided in one of the manipulator and the driving device, wherein the controller is configured to perform a first step of confirming that the driving device operates normally according to electric power on the basis of an output of the first sensor, and a second step of confirming that the manipulator is connected to the driving device on the basis of an output of the second sensor, the first step includes checking whether the first sensor is normal, and the second step includes checking whether the second sensor is normal on the basis of the output of the first sensor that has been confirmed to be normal in the first step and the output of the second sensor.

2. The manipulator system according to claim 1, wherein the driving device includes the actuator that generates a driving force with the electric power, and, in the second step, if the output of the second sensor indicates that the manipulator is connected to the driving device and if the output of the first sensor changes in response to the driving force, it is determined that the second sensor is normal.

3. The manipulator system according to claim 2, wherein the manipulator includes a movable portion and a driving wire that transmits the driving force to the movable portion, the actuator includes a motor that generates a rotational force as the driving force, the first sensor is a torque sensor that detects a torque of the motor, and the second sensor is a coupling sensor that detects coupling between the driving wire and the motor.

4. The manipulator system according to claim 3, wherein the manipulator includes a pulley around which an end of the driving wire is wound and which is rotatably supported, and a coupling part fixed to a proximal end of the pulley, the driving device includes a shaft rotated by the motor and a coupled part fixed to a distal end of the shaft and configured to be fitted with the coupling part, the shaft is supported so as to be movable forward and backward along a rotation axis of the shaft, the shaft is displaced along the rotation axis when the coupling part is fitted with the coupled part, and the coupling sensor detects fitting between the coupling part and the coupled part on the basis of displacement of the shaft.

5. The manipulator system according to claim 1, wherein in the second step, from the output of one of the first sensor and the second sensor, an estimated output of the other of the first sensor and the second sensor is calculated, and, if a difference between the output of the other of the first sensor and the second sensor and the estimated output of the other is within a predetermined range, it is determined that the second sensor is normal.

6. The manipulator system according to claim 5, wherein the manipulator includes a movable portion and a driving wire that transmits a driving force to the movable portion, the first sensor is a torque sensor that detects a torque of the actuator provided in the driving device, and the second sensor is a tension sensor that detects a tension of the driving wire.

7. The manipulator system according to claim 1, wherein the controller is further configured to perform a third step of confirming that a movable portion of the manipulator operates normally according to the driving force transmitted from the driving device on the basis of an output of a third sensor, and the third step includes checking whether the third sensor is normal on the basis of the output of the first sensor that has been confirmed to be normal in the first step and the output of the third sensor.

8. The manipulator system according to claim 7, wherein in the third step, from the output of one of the first sensor and the third sensor, an estimated output of the other of the first sensor and the third sensor is calculated, and if a difference between the output of the other of the first sensor and the third sensor and the estimated output of the other is within a predetermined range, it is determined that the third sensor is normal.

9. The manipulator system according to claim 8, wherein the manipulator includes a movable portion and a driving wire that transmits the driving force to the movable portion, the first sensor is a torque sensor that detects a torque of the actuator provided in the driving device, and the third sensor is a tension sensor that detects a tension of the driving wire.

10. A control method for controlling a manipulator system, the manipulator system comprising a manipulator and a driving device comprising least one actuator, the manipulator is detachably connected to the driving device and the driving device electrically drives the manipulator, the control method comprising:

performing a first step of confirming that the driving device operates normally according to electric power on the basis of an output of a first sensor; and performing a second step of confirming that the manipulator is connected to the driving device on the basis of an output of a second sensor, wherein the first step includes checking whether the first sensor is normal, and the second step includes checking whether the second sensor is normal on the basis of the output of the first sensor that has been confirmed to be normal in the first step and the output of the second sensor.

11. The control method according to claim 10, wherein in the second step, if the output of the second sensor indicates that the manipulator is connected to the driving device and if the output of the first sensor changes in response to a driving force generated by the driving device with the electric power, it is determined that the second sensor is normal.

12. The control method according to claim 10, wherein in the second step, from the output of one of the first sensor and the second sensor, an estimated output of the other of the first sensor and the second sensor is calculated, and if a difference between the output of the other of the first sensor and the second sensor and the estimated output of the other is within a predetermined range, it is determined that the second sensor is normal.

13. The control method according to claim 10, further comprising performing a third step of confirming that a movable portion of the manipulator operates normally according to the driving force transmitted from the driving device on the basis of an output of a third sensor, wherein the third step includes checking whether the third sensor is normal on the basis of the output of the first sensor that has been confirmed to be normal in the first step and the output of the third sensor.

14. The control method according to claim 13, wherein in the third step, from the output of one of the first sensor and the third sensor, an estimated output of the other of the first sensor and the third sensor is calculated, and if a difference between the output of the other of the first sensor and the third sensor and the estimated output of the other is within a predetermined range, it is determined that the third sensor is normal.

15. A control device comprising:

a controller comprising hardware, the controller is configured to control a manipulator system, the manipulator system comprising a manipulator and a driving device comprising at least one actuator, the manipulator is detachably connected to the driving device and the driving device electrically drives the manipulator, wherein the controller is configured to perform a first step of confirming that the driving device operates normally according to electric power on the basis of an output of a first sensor, and a second step of confirming that the manipulator is connected to the driving device on the basis of an output of a second sensor, the first step includes checking whether the first sensor is normal, and the second step includes checking whether the second sensor is normal on the basis of the output of the first sensor that has been confirmed to be normal in the first step and the output of the second sensor.

16. The control device according to claim 15, wherein in the second step, if the output of the second sensor indicates that the manipulator is connected to the driving device and if the output of the first sensor changes in response to a driving force generated by the driving device with the electric power, it is determined that the second sensor is normal.

* * * * *